(12) United States Patent
Wagner et al.

(10) Patent No.: US 7,001,890 B1
(45) Date of Patent: Feb. 21, 2006

(54) PHARMACEUTICAL COMPOSITIONS COMPRISING A POLYNUCLEOTIDE AND OPTIONALLY AN ANTIGEN ESPECIALLY FOR VACCINATION

(75) Inventors: Hermann Wagner, Eching (DE); Grayson Lipford, Munich (DE); Klaus Heeg, Marburg-Michelbach (DE)

(73) Assignee: Coley Pharmaceutical GmbH, Langenfeld (DE)

( * ) Notice: Subject to any disclaimer, the term of this patent is extended or adjusted under 35 U.S.C. 154(b) by 0 days.

(21) Appl. No.: 09/355,254

(22) PCT Filed: Jan. 23, 1998

(86) PCT No.: PCT/EP98/00367

§ 371 (c)(1),
(2), (4) Date: Feb. 22, 2000

(87) PCT Pub. No.: WO98/32462

PCT Pub. Date: Jul. 30, 1998

(30) Foreign Application Priority Data

Jan. 23, 1997 (EP) .................................. 97101019

(51) Int. Cl.
*A01N 43/04* (2006.01)
*A01N 61/00* (2006.01)
*C12Q 1/68* (2006.01)
*C12P 19/34* (2006.01)
*C07H 21/04* (2006.01)

(52) U.S. Cl. ...................... 514/44; 435/6; 435/91.1; 514/1; 514/2; 536/23.1; 536/24.1

(58) Field of Classification Search ............... 536/23.1, 536/24.5, 24.1; 530/300, 350, 351; 514/44, 514/1, 2; 435/6, 69.1, 91.1, 455, 91.31, 458, 435/375

See application file for complete search history.

(56) References Cited

U.S. PATENT DOCUMENTS 3,906,092 A 9/1975 Hilleman et al. ............. 424/89

(Continued)

FOREIGN PATENT DOCUMENTS

EP 0 092 574 B1 11/1983

(Continued)

OTHER PUBLICATIONS

Agrawal et al. Molecular Medicine Today, Feb. 2000, vol. 6, pp 72-81.*

(Continued)

*Primary Examiner*—Sean McGarry
*Assistant Examiner*—Jane Zara
(74) *Attorney, Agent, or Firm*—Wolf, Greenfield & Sacks, P.C.

(57) ABSTRACT

The present invention relates to pharmaceutical compositions comprising at least one fragment of a polynucleotide, preferably at least one antigen, and optionally a pharmaceutically acceptable carrier and/or diluent. In accordance with the present invention was found that the introduction of the pharmaceutical composition into vertebrates will achieve regulation of growth, induction of cellular transcription and translation, protein synthesis, protein expression or protein secretion. The pharmaceutical compositions are useful in vaccination protocols but also in any other therapeutic situation in which immunomodulation is of benefit, such as sub-optimal immune responses, reaction to pathogens, tolerance or autoimmunity.

34 Claims, 7 Drawing Sheets

Figure 1:
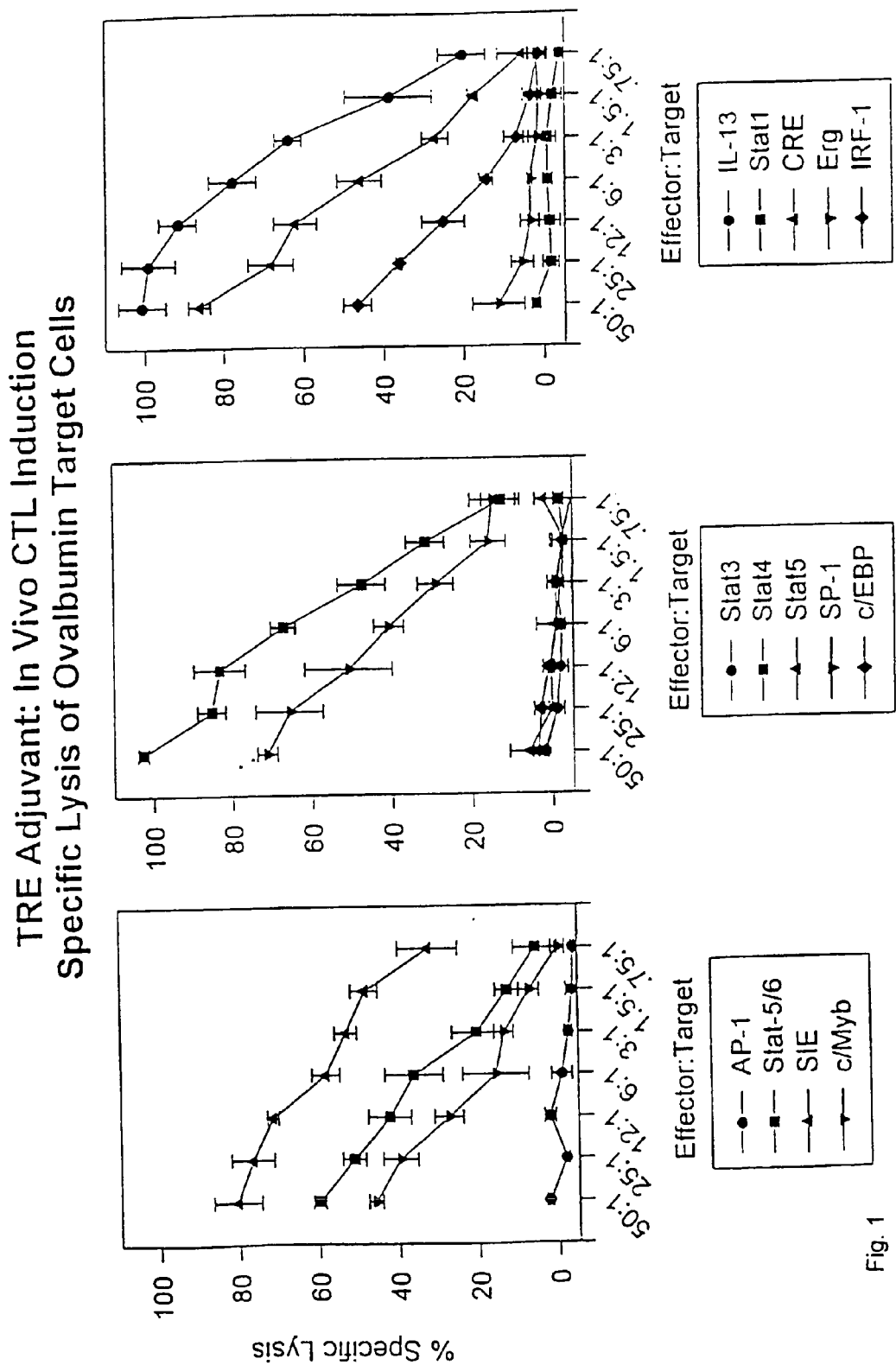

TRE Adjuvant: In Vivo CTL Induction
Specific Lysis of Ovalbumin Target Cells

U.S. PATENT DOCUMENTS

| | | | |
|---|---|---|---|
| 5,248,670 A | 9/1993 | Draper et al. | 514/44 |
| 5,328,987 A | 7/1994 | Maliszewski | 530/350 |
| 5,585,479 A | 12/1996 | Hoke et al. | 536/24.5 |
| 5,591,825 A * | 1/1997 | McKnight et al. | 530/350 |
| 5,616,489 A * | 4/1997 | Levy | 435/325 |
| 5,641,486 A * | 6/1997 | Hinrichs et al. | 424/139.1 |
| 5,663,153 A | 9/1997 | Hutcherson et al. | 514/44 |
| 5,679,647 A | 10/1997 | Carson et al. | |
| 5,723,335 A * | 3/1998 | Hutcherson et al. | 435/375 |
| 5,780,448 A * | 7/1998 | Davis | 514/44 |
| 5,786,189 A | 7/1998 | Locht et al. | |
| 5,834,188 A * | 11/1998 | Harada et al. | 435/6 |
| 5,849,719 A | 12/1998 | Carson et al. | 514/44 |
| 5,912,168 A * | 6/1999 | Watson et al. | 435/320.1 |
| 6,057,299 A * | 5/2000 | Henderson | 514/44 |
| 6,194,388 B1 | 2/2001 | Krieg et al. | |
| 6,207,646 B1 | 3/2001 | Krieg et al. | |
| 6,214,804 B1 | 4/2001 | Felgner et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 * | 6/2002 | Davis et al. | 424/278.1 |
| 6,429,199 B1 | 8/2002 | Krieg et al. | |
| 6,653,292 B1 | 11/2003 | Krieg et al. | |
| 6,727,230 B1 | 4/2004 | Hutcherson et al. | |
| 2001/0044416 A1 | 11/2001 | McCluskie et al. | |
| 2002/0064515 A1 | 5/2002 | Krieg et al. | |
| 2002/0091097 A1 | 7/2002 | Bratzler et al. | |
| 2002/0156033 A1 | 10/2002 | Bratzler et al. | |
| 2002/0164341 A1 | 11/2002 | Davis et al. | |
| 2002/0165178 A1 | 11/2002 | Schetter et al. | |
| 2002/0198165 A1 | 12/2002 | Bratzler et al. | |
| 2003/0026782 A1 | 2/2003 | Krieg et al. | |
| 2003/0026801 A1 | 2/2003 | Weiner et al. | |
| 2003/0050261 A1 | 3/2003 | Krieg et al. | |
| 2003/0050263 A1 | 3/2003 | Krieg et al. | |
| 2003/0050268 A1 | 3/2003 | Krieg et al. | |
| 2003/0055014 A1 | 3/2003 | Bratzler | |
| 2003/0087848 A1 | 5/2003 | Bratzler et al. | |
| 2003/0091599 A1 | 5/2003 | Davis et al. | |
| 2003/0100527 A1 | 5/2003 | Krieg et al. | |
| 2003/0104523 A1 | 6/2003 | Lipford et al. | |
| 2003/0139364 A1 | 7/2003 | Krieg et al. | |
| 2003/0148316 A1 | 8/2003 | Lipford et al. | |
| 2003/0148976 A1 | 8/2003 | Krieg et al. | |
| 2003/0166001 A1 | 9/2003 | Lipford | |
| 2003/0181406 A1 | 9/2003 | Schetter et al. | |
| 2003/0191079 A1 | 10/2003 | Krieg et al. | |
| 2003/0212026 A1 | 11/2003 | Krieg et al. | |
| 2003/0224010 A1 | 12/2003 | Davis et al. | |
| 2003/0232074 A1 | 12/2003 | Lipford et al. | |
| 2004/0009949 A1 | 1/2004 | Krieg | |
| 2004/0030118 A1 | 2/2004 | Wagner et al. | |
| 2004/0053880 A1 | 3/2004 | Krieg | |
| 2004/0067905 A1 | 4/2004 | Krieg | |
| 2004/0087534 A1 | 5/2004 | Krieg et al. | |
| 2004/0087538 A1 | 5/2004 | Krieg et al. | |
| 2004/0092472 A1 | 5/2004 | Krieg | |
| 2004/0106568 A1 | 6/2004 | Krieg et al. | |
| 2004/0131628 A1 | 7/2004 | Bratzler et al. | |
| 2004/0132685 A1 | 7/2004 | Krieg et al. | |
| 2004/0142469 A1 | 7/2004 | Krieg et al. | |
| 2004/0143112 A1 | 7/2004 | Krieg et al. | |
| 2004/0147468 A1 | 7/2004 | Krieg et al. | |
| 2004/0152649 A1 | 8/2004 | Krieg | |
| 2004/0152656 A1 | 8/2004 | Krieg et al. | |
| 2004/0152657 A1 | 8/2004 | Krieg et al. | |
| 2004/0162258 A1 | 8/2004 | Krieg et al. | |
| 2004/0162262 A1 | 8/2004 | Krieg et al. | |
| 2004/0167089 A1 | 8/2004 | Krieg et al. | |
| 2004/0171150 A1 | 9/2004 | Krieg et al. | |
| 2004/0171571 A1 | 9/2004 | Krieg et al. | |
| 2004/0181045 A1 | 9/2004 | Krieg et al. | |
| 2004/0198688 A1 | 10/2004 | Krieg et al. | |

FOREIGN PATENT DOCUMENTS

| | | |
|---|---|---|
| EP | 0 468 520 A3 | 1/1992 |
| EP | 0 302 758 A1 | 3/1994 |
| WO | WO 91/12811 | 9/1991 |
| WO | WO 92/03456 | 3/1992 |
| WO | WO 92/18522 | 10/1992 |
| WO | WO 92/21353 | 12/1992 |
| WO | WO 94/19945 | 9/1994 |
| WO | WO 95/05853 | 3/1995 |
| WO | WO 95/26204 | 10/1995 |
| WO | WO 96/02555 | 2/1996 |
| WO | WO96/02560 A1 | 2/1996 |
| WO | WO 96/12823 * | 5/1996 |
| WO | WO 96/17960 * | 6/1996 |
| WO | WO 96/35782 | 11/1996 |
| WO | WO97/28259 A1 | 8/1997 |
| WO | WO 98/14210 | 4/1998 |
| WO | WO98/16247 A1 | 4/1998 |
| WO | WO 98/18810 | 5/1998 |
| WO | WO 98/37919 | 9/1998 |
| WO | WO 98/40100 | 9/1998 |
| WO | WO 98/52581 | 11/1998 |
| WO | WO98/55495 A2 | 12/1998 |
| WO | WO99/51259 A2 | 10/1999 |
| WO | WO99/56755 A1 | 11/1999 |
| WO | WO99/58118 A2 | 11/1999 |
| WO | WO99/61056 A2 | 12/1999 |
| WO | WO00/06588 A1 | 2/2000 |
| WO | WO00/14217 A3 | 3/2000 |
| WO | WO00/67023 A1 | 11/2000 |
| WO | WO01/22972 A2 | 4/2001 |
| WO | WO01/22990 | 4/2001 |
| WO | WO 02/069369 A2 | 9/2002 |
| WO | WO 2004/007743 A2 | 1/2004 |
| WO | WO 2004/039829 A2 | 5/2004 |

OTHER PUBLICATIONS

Pihl-Carey, I. BioWorld Today, Dec. 1999. vol. 10, PP 1-2.*
Crooke, S. Antisense Res. and Application, 1998, Chap. 1, pp 1-50. Springer-Verlag, Pub.*
Chirila et al. Biomaterials, 2002, vol. 23, pp 321-342.*
Palu et al. J. Biotech. 1999. vol. 68, pp 1-13.*
Branch, A. Trends in Biochem. Sci, Feb. 1998. vol. 358, pp 489-497.*
Weiner, G. J. Leukocyte Biology, Oct. 2000, vol. 68, pp 455-462.*
Blackshear, P. Toxicologic Path. 2001, vol. 29, No. 1, pp 105-116.*
McCluskie, et al. Molecular Medicine, 1999, vol. 5, pp 287-300.*
Cha, Y. et al. J. Biol. Chem. vol. 269, No. 7. pp. 5279-5287 (1994).*
Dolganov, G. et al. Blood. vol. 87, No. 8, pp. 3316-3326 (1996).*
Stanford, W. et al. Immunogenetics,. vol. 35, pp. 408-411 (1992).*
Chu, R. et al. J. Exp. Med. vol. 186, No. 10, pp. 1623-1631 (1997).*
Ballas ZK et al., Induction of NK activity in murine and human cells by CpG motifs in oligodeoxynucleotides and bacterial DNA. *J. Immunol.* Sep. 1, 1996;157(5):1840-5.
Bayever E et al., Systemic administration of a phosphorothioate oligonucleotide with a sequence complementary to p53 for acute myelogenous leukemia and myelodysplastic syndrome: initial results of a phase I trial. *Antisense Res Dev.* 1993 Winter;3(4):383-90.

Boggs RT et al., Characterization and modulation of immune stimulation by modified oligonucleotides. *Antisense Nucleic Acid Drug Dev.* Oct. 1997;7(5):461-71.

Branda RF et al., Amplification of antibody production by phosphorothioate oligodeoxynucleotides. *J. Lab Clin Med.* Sep. 1996;128(3):329-38.

Branda RF et al., Immune stimulation by an antisense oligomer complementary to the rev gene of HIV-1. *Biochem Pharmacol.* May 25, 1993;45(10):2037-43.

Chace JH et al., Regulation of differentiation in CD5+ and conventional B cells. Sensitivity to LPS-induced differentiation and interferon-gamma-mediated inhibition of differentiation. *Clin Immunol Immunopathol.* Sep. 1993;68(3):327-32.

Chang YN et al., The palindromic series I repeats in the simian cytomegalovirus major immediate-early promoter behave as both strong basal enhancers and cyclic AMP response elements. *J. Virol.* Jan. 1990;64(1):264-77.

Chu RS et al., CpG oligodeoxynucleotides act as adjuvants that switch on T helper 1 (Th1) immunity. *J Exp Med.* Nov. 17, 1997;186(10):1623-31.

Cowdery JS et al., Bacterial DNA induces NK cells to produce IFN-gamma in vivo and increases the toxicity of lipopolysaccharides. *J. Immunol.* Jun. 15, 1996;156(12):4570-5.

Davis HL et al., CpG DNA is a potent enhancer of specific immunity in mice immunized with recombinant hepatitis B surface antigen. *J. Immunol.* Jan. 15, 1998;160(2):870-6.

Gramzinski RA et al., Immune response to a hepatitis B DNA vaccine in Aotus monkeys: a comparison of vaccine formulation, route, and method of administration. *Mol Med.* Feb. 1998;4(2):109-18.

Halpern MD et al., Bacterial DNA induces murine interferon-gamma production by stimulation of interleukin-12 and tumor necrosis factor-alpha. *Cell Immunol.* Jan. 10, 1996;167(1):72-8.

Hoeffler JP et al., Identification of multiple nuclear factors that interact with cyclic adenosine 3',5'-monophosphate response element-binding protein and activating transcription factor-2 by protein-protein interactions. *Mol Endocrinol.* Feb. 1991;5(2):256-66.

Kataoka T et al., Immunotherapeutic potential in guinea-pig tumor model of deoxyribonucleic acid from Mycobacterium bovis BCG complexed with poly-L-lysine and carboxymethylcellulose. *Jpn J Med Sci Biol.* Oct. 1990;43(5):171-82.

Klinman DM et al., Contribution of CpG motifs to the immunogenicity of DNA vaccines. *J. Immunol.* Apr. 15, 1997;158(8):3635-9.

Klinman DM et al., Immune recognition of foreign DNA: a cure for bioterrorism? *Immunity.* Aug. 1999;11(2):123-9.

Krieg AM et al., Phosphorothioate oligodeoxynucleotides: antisense or anti-protein? *Antisense Res Dev.* 1995 Winter;5(4):241.

Kreig AM et al., The role of CpG dinucleotides in DNA vaccines. *Trends Microbiol.* Jan. 1998;6(1):23-7.

Krieg AM, CpG DNA: a pathogenic factor in systemic lupus erythematosus? *J Clin Immunol.* Nov. 1995;15(6):284-92.

Krieg AM, Leukocyte stimulation by oligodeoxynucleotides. In: *Applied Antisense Oligonucleotide Technology,* Stein CA and Kreig Am, eds., New York: Wiley-Liss, 1998; pp. 431-438.

Lipford GB et al., Bacterial DNA as immune cell activator. *Trends Microbiol.* Dec. 1998;6(12):496-500.

Lipford GB et al., CpG-containing synthetic oligonucleotides promote B and cytotoxic T cell responses to protein antigen: a new class of vaccine adjuvants. *Eur J Immunol.* Sep. 1997;27(9):2340-4.

Lipford GB et al., Immunostimulatory DNA: sequence-dependent production of potentially harmful or useful cytokines. *Eur J Immunol.* Dec. 1997;27(12):3420-6.

Moldoveanu Z et al., CpG DNA, a novel immune enhancer for systemic and mucosal immunization with influenza virus. *Vaccine.* Jul. 1998;16(11-12):1216-24.

Paca-Uccaralertkun S et al., In vitro selection of DNA elements highly responsive to the human T-cell lymphotropic virus type I transcriptional activator, Tax. *Mol Cell Biol.* Jan. 1994;14(1):456-62.

Pisetsky DS et al., Stimulation of in vitro proliferation of murine lymphocytes by synthetic oligodeoxynucleotides. *Mol Biol Rep.* Oct. 1993;18(3):217-21.

Pisetsky DS, Immunologic consequences of nucleic acid therapy. *Antisense Res Dev.* 1995 Fall;5(3):219-25.

Pisetsky DS, The immunologic properties of DNA. *J. Immunol.* Jan. 15, 1996;156(2):421-3.

Raz E et al., Preferential induction of a Th1 immune response and inhibition of specific IgE antibody formation by plasmid DNA immunization. *Proc Natl Acad Sci U S A.* May 14, 1996;93(10):5141-5.

Sparwasser T et al., Macrophages sense pathogens via DNA motifs: induction of tumor necrosis factor-alpha-mediated shock. *Eur J Immunol.* Jul. 1997;27(7):1671-9.

Sparwasser T et al., Bacterial DNA and immunostimulatory CpG oligonucleotides trigger maturation and activation of murine dendritic cells. *Eur J Immunol.* Jun. 1998;28(6):2045-54.

Sun S et al., Mitogenicity of DNA from different organisms for murine B cells. *J Immunol.* Oct. 1, 1997;159(7):3119-25.

Threadgill DS et al., Mitogenic synthetic polynucleotides suppress the antibody response to a bacterial polysaccharide. *Vaccine.* Jan. 1998;16(1):76-82.

Tsukada J et al., Transcription factors NF-IL6 and CREB recognize a common essential site in the human prointerleukin 1 beta gene. *Mol Cell Biol.* Nov. 1994;14(11):7285-97.

Weiner GJ et al., Immunostimulatory oligodeoxynucleotides containing the CpG motif are effective as immune adjuvants in tumor antigen immunization. *Proc Natl Acad Sci U S A.* Sep. 30, 1997;94(20):10833-7.

Yi AK et al., IFN-gamma promotes IL-6 and IgM secretion in response to CpG motifs in bacterial DNA and oligodeoxynucleotides. *J Immunol.* Jan. 15, 1996;156(2):558-64.

Adya N et al., Expansion of CREB's DNA recognition specificity by Tax results from interaction with Ala-Ala-Arg at positions 282-284 near the conserved DNA-binding domain of CREB. *Proc Natl Acad Sci USA* 91(12):5642-6, Jun. 7, 1994.

Arany Z et al., E1A-associated p300 and CREB-associated CBP belong to a conserved family of coactivators. *Cell* 77(6):799-800, Jun. 17, 1994.

Arias J et al., Activation of cAMP and mitogen responsive genes relies on a common nuclear factor. *Nature* 370:226-9, Jul. 21, 1994.

Asiedu CK et al., Binding of AP-1/CREB proteins and of MDBP to contiguous sites downstream of the human TGFbeta 1 gene. *Biochim Biophys Acta* 1219(1):55-63, Sep. 13, 1994.

Azad RF et al., Antiviral activity of a phosphorothioate oligonucleotide complementary to RNA of the human cytomegalovirus major immediate-early region. *Antimicrob Agents Chemother* 37(9):1945-54, Sep. 1993.

Azuma I et al., Biochemical and immunological studies on cellular components of tubercle bacilli. *Kekkaku* 67(9):625-631, 1992.

Blaxter ML et al., Genes expressed in *Brugia malayi* infective third stage Iarvae. *Mol Biochem Parasitol* 77(1):77-93, Apr. 1996.

Briskin M et al., Lipopolysaccharide-unresponsive mutant pre-B-cell lines blocked in NF-kappa B activation. *Mol Cell Biol* 10(1):422-5, Jan. 1990.

Crosby SD et al., The early response gene NGFI-C encodes a zinc finger transcriptional activator and is a member of the GCGGGGGCG (GSG) element-binding protein family. *Mol Cell Biol* 11(8):3835-41, Aug. 1991.

Crystal RG, Transfer of genes to humans: early lessons and obstacles to success. *Science* 270(5235):404-10, Oct. 20, 1995.

Du W and Maniatis T, An ATF/CREB binding site is required for virus induction of the human interferon beta gene. *Proc Natl Acad Sci USA* 89(6):2150-4, Mar. 1992.

Du W et al., Mechanisms of transcriptional synergism between distinct virus-inducible enhancer elements. *Cell* 74(5):887-98, Sep. 10, 1993.

Englisch et al., Chemically modified oligonucleotides as probes and inhibitors. *Angew Chem Int Ed Engl* 30:613-629, 1991.

Ferreri K et al., The cAMP-regulated transcription factor CREB interacts with a component of the TFIID Complex. *Proc Natl Acad Sci USA* 91(4):1210-3, Feb. 1994.

Gray GD et al., Antisense DNA inhibition of tumor growth induced by c-Ha-ras oncogene in nude mice. *Cancer Res* 53(3):577-80, Feb. 1, 1993.

Highfield PE, Sepsis: the more, the murkier. *Biotechnology* 12(8):828, Aug. 1994.

Himes SR et al., HTLV-1 tax activation of the GM-CSF and G-CSF promoters requires the interaction of NF-κB with other transcription factor families. *Oncogene* 8(12):3189-97, Dec. 1993.

Huang D et al., Promoter activity of the proliferating-cell nuclear antigen gene is associated with inducible CRE-binding proteins in interleukin 2-stimulated T lymphocytes. *Mol Cell Biol* 14(6):4233-43, Jun. 1994.

Iguchi-Ariga SM and Schaffner W, CpG methylation of the cAMP-responsive enhancer/promoter sequence TGACGTCA abolishes specific factor binding as well as transcriptional activation. *Genes Dev* 3(5):612-9, May 1989.

Kataoka T et al., Antitumor activity of synthetic oligonucleotides with sequences from cDNA encoding proteins of *Mycobacterium bovis* BCG. *Jpn J Cancer Res* 83(3):244-7, Mar. 1992.

Kimura Y et al., Binding of oligoguanylate to scavenger receptors is required for oligonucleotides to augment NK cell activity and induce IFN. *J Biochem* (Tokyo) 116(5):991-4, Nov. 1994.

Kline JN et al., CpG motif oligonucleotides are effective in prevention of eosinophilic inflammation in a murine model of asthma. *J. Invest Med* 44(7):380A, 1996.

Kline JN et al., Immune redirection by CpG oligonucleotides. Conversion of a Th2 response to a Th1 response in a murine model of asthma. *J. Invest Med* 45(3):282A, 1997.

Kline JN et al., CpG oligonucleotides can reverse as well as prevent TH2-mediated inflammation in a murine model of asthma. *J Invest Med* 45(7):298A, 1997.

Klinman DM et al., CpG motifs present in bacteria DNA rapidly induce lymphocytes to secrete interleukin 6, interleukin 12, and interferon gamma. *Proc Natl Acad Sci USA* 93(7):2879-83, Apr. 2, 1996.

Krajewski W et al., A monomeric derivative of the cellular transcription factor CREB functions as a constitutive activator. *Mol Cell Biol* 14(11):7204-10, Nov. 1994.

Krieg AM, An innate immune defense mechanism based on the recognition of CpG motifs in microbial DNA. *J Lab Clin Med* 128(2):128-33, Aug. 1996.

Krieg AM et al., A role for endogenous retroviral sequences in the regulation of lymphocyte activation. *J Immunol* 143(8):2448-51, Oct. 15, 1989.

Krieg AM et al., CpG motifs in bacterial DNA trigger direct B-cell activation. *Nature* 374:546-9, Apr. 6, 1995.

Krieg AM et al., Oligodeoxynucleotide modifications determine the magnitude of B cell stimulation by CpG motifs. *Antisense Nucleic Acid Drug Dev* 6(2):133-9, Summer 1996.

Krieg AM et al., Uptake of oligodeoxyribonucleotides by lymphoid cells is heterogeneous and inducible. *Antisense Res Dev* 1(2):161-71, Summer 1991.

Kuramoto E et al., Oligonucleotide sequences required for natural killer cell activation. *Jpn J Cancer Res* 83(11):1128-31, Nov. 1992.

Kwok RP et al., Nuclear protein CBP is a coactivator for the transcription factor CREB. *Nature* 370:223-6, Jul. 21, 1994.

Lee KA and Masson N, Transcriptional regulation by CREB and its relatives. *Biochim Biophys Acta* 1174(3):221-33, Sep. 23, 1993.

Leonard GA et al., Conformation of guanine-8-oxoadenine base pairs in the crystal structure of d(CGCGAATT(O8A)GCG). *Biochemistry* 31(36):8415-20, Sep. 15, 1992.

Liu F and Green MR, Promoter targeting by adenovirus E1a through interaction with different cellular DNA-binding domains. *Nature* 368:520-5, Apr. 7, 1994.

McIntyre KW et al., A sense phosphorothioate oligonucleotide directed to the initiation codon of transcription factor NF-kappa B p65 causes sequence-specific immune stimulation. *Antisense Res Dev* 3(4):309-22, Winter 1993.

Messina JP et al., The influence of DNA structure on the in vitro stimulation of murine lymphocytes by natural and synthetic polynucleotide antigens. *Cell Immunol* 147(1):148-57, Mar. 1993.

Messina JP et al., Stimulation of in vitro murine lymphocyte proliferation by bacterial DNA. *J Immunol* 147(6):1759-64, Sep. 15, 1991.

Mottram JC et al., A novel CDC2-related protein kinase from Leishmania mexicana, LmmCRK1, is post-translationally regulated during the life cycle. *J Biol Chem* 268(28):21044-52, Oct. 5, 1993.

Nyce JW and Metzger WJ, DNA antisense therapy for asthma in an animal model. *Nature* 385(6618):721-5, Feb. 20, 1997.

Peterson, M., et al., Transcription Factors: A New Frontier in Pharmaceutical Development, Bio Pharm, 47:1:127-128.

Pisetsky DS and Reich CF, Stimulation of murine lymphocyte proliferation by a phosphorothioate oligonucleotide with antisense activity for herpes simplex virus. *Life Sci* 54(2):101-7, 1994.

Rojanasakul Y, Antisense oligonucleotide therapeutics: drug delivery and targeting. Adv Drug Delivery Rev 18:115-131, 1996.

Roman M et al., Immunostimulatory DNA sequences function as T helper-1-promoting adjuvants. *Nat Med* 3(8):849-54, Aug. 1997.

Sato Y et al., Immunostimulatory DNA sequences necessary for effective intradermal gene immunization. *Science* 273 (5273):352-4, Jul. 19, 1996.

Schnell N and Entian KD, Identification and characterization of a *Saccharomyces cerevisiae* gene (PAR1) conferring resistance to iron chelators. *Eur J Biochem* 200(2):487-93, Sep. 1, 1991.

Stein CA and Cohen JS, Oligodeoxynucleotides as inhibitors of gene expression: a review. *Cancer Res* 48(10):2659-68, May 15, 1988.

Stull RA and Szoka FC Jr, Antigene, ribozyme and aptamer nucleic acid drugs: progress and prospects. *Pharm Res* 12(4):465-83, Apr. 1995.

Tanaka T et al., An antisense oligonucleotide complementary to a sequence in I gamma 2b increases gamma 2b germline transcripts, stimulates B cell DNA synthesis, and inhibits immunoglobulin secretion. *J Exp Med* 175(2):597-607, Feb. 1992.

Tokunaga T et al., Synthetic oligonucleotides with particular base sequences from the cDNA encoding proteins of *Mycobacterium bovis* BCG induce interferons and activate natural killer cells. *Microbiol Immunol* 36(1):55-66, 1992.

Tokunaga T et al., A synthetic single-stranded DNA, poly (dG,dC), induces interferon-alpha/beta and -gamma, augments natural killer activity, and suppresses tumor growth. *Jpn J Cancer Res* 79(6):682-6, Jun. 1988.

Uhlmann E and Peyman A, Antisense oligonucleotides: a new therapeutic principle. *Chem Rev* 90(4):543-84, Jun. 1990.

Wagner RW, Gene inhibition using antisense oligodeoxynucleotides. *Nature* 372(6504):333-5, Nov. 24, 1994.

Wallace RB and Miyada CG, Oligonucleotide probes for the screening of recombinant DNA libraries. *Methods Enzymol* 152:432-442, 1987.

Weiss R, Upping the antisense ante: scientists bet on profits from reverse genetics. *Science News* 139:108-109, Feb. 16, 1991.

Whalen RG, DNA vaccines for emerging infectious diseases: what if? *Emerg Infect Dis* 2(3):168-75, 1996.

Wu-Pong S, Oligonucleotides: opportunities for drug therapy and research. *Pharm Technol* 18:102-114, Oct. 1994.

Xie H et al., Induction of CREB activity via the surface Ig receptor of B cells. *J Immunol* 151(2):880-9, Jul. 15, 1993.

Yamamoto S, Mode of action of oligonucleotide fraction extracted from *Mycobacterium bovis* BCG. *Kekkaku* 69(9): 571-4, Sep. 1994.

Yamamoto S et al., DNA from bacteria, but not from vertebrates, induces interferons, activates natural killer cells and inhibits tumor growth. *Microbiol Immunol* 36(9):983-97, 1992.

Yamamoto S et al., Unique palindromic sequences in synthetic oligonucleotides are required to induce IFN and augment IFN-mediated natural killer activity. *J Immunol* 148(12):4072-6, 1992.

Yamamoto T et al., Ability of oligonucleotides with certain palindromes to induce interferon production and augment natural killer cell activity is associated with their base length. *Antisense Res Dev* 4(2):119-22, Summer 1994.

Yamamoto T et al., Lipofection of synthetic oligodeoxyribonucleotide having a palindromic sequence of AACGTT to murine splenocytes enhances interferon production and natural killer activity. *Microbiol Immunol* 38(10):831-6, 1994.

Yamamoto T et al., Synthetic oligonucleotides with certain palindromes stimulate interferon production of human peripheral blood lymphocytes in vitro. *Jpn J Cancer Res* 85(8):775-9, Aug. 1994.

Yi AK et al., Rapid immune activation by CpG motifs in bacterial DNA, Systemic induction of IL-6 transcription through an antioxidant-sensitive pathway. *J Immunol* 157 (12):5394-402, Dec. 15, 1996.

Zhao Q et al., Comparison of cellular binding and uptake of antisense phosphodiester, phosphorothioate, and mixed phosphorothioate and methylphosphonate oligonucleotides. *Antisense Res Dev* 3(1):53-66, Spring 1993.

Zhao Q et al., Stage-specific oligonucleotide uptake in murine bone marrow B-cell precursors. *Blood* 84(11):3660-6, Dec. 1, 1994.

New England Biolabs Catalog, 1988-1989, item #1230.

* cited by examiner

PHARMACEUTICAL COMPOSITIONS COMPRISING A POLYNUCLEOTIDE AND OPTIONALLY AN ANTIGEN ESPECIALLY FOR VACCINATION

This application claims priority to PCT Patent Application No. PCT/EP98/00367, filed Jan. 23, 1998, and published in English as WO 98/32462, which in turn claims priority to EP Patent Application No. EP 97101019.4, filed Jan. 23, 1997.

The present invention relates to pharmaceutical compositions comprising at least one fragment of a polynucleotide, preferably at least one antigen, and optionally a pharmaceutically acceptable carrier and/or diluent. In accordance with the present invention was found that the introduction of the pharmaceutical composition into vertebrates will achieve regulation of growth, induction of cellular transcription and translation, protein synthesis, protein expression or protein secretion. The pharmaceutical compositions are useful in vaccination protocols but also in any other therapeutic situation in which immunomodulation is of benefit, such as sub-optimal immune responses, reaction to pathogens, tolerance or autoimmunity.

It is known that cells of the immune system are exported from the bone marrow and undergo a series of differentiation events which confer upon them the capacity to recognize and control foreign pathogens and cancer cells by discriminating between self versus non-self. These differentiation and education events are tightly controlled by cell surface receptor engagement via intracellular signal transduction and the milieu of autocrine, paracrine and endocrine soluble ligands, typically referred to as cytokines. Cell to cell interaction occurs in discrete locations such as the thymus, spleen or lymph nodes but also in the periphery. The system thus balances receptor and cytokine input signals to regulate cellular proliferation, differentiation and maturation of immune effector cells [Paul, Cell, 57:521 (1989)]. Through outside intervention the immune system can be manipulated, namely enhanced, e.g. by vaccination or cytokine therapies, or suppressed, e.g. by drug intervention or cytokine therapies.

The immune system of vertebrates consists of several interacting components. The best characterized and most important parts are the humoral and cellular (cytolytic) branches. Humoral immunity involves antibodies, proteins which are secreted into the body fluids and which directly recognize an antigen. The cellular system, in contrast, relies on special cells which recognize and kill other cells which are producing foreign antigens. This basic functional division reflects two different strategies of the immune defense. Humoral immunity is mainly directed at antigens which are exogenous to the host's somatic cells or on the surface of cells whereas the cellular system responds to antigens which are actively synthesized within cells or derived from phagocytosed exogenous antigens.

Antibody molecules, the effectors of humoral immunity, are secreted by special B lymphoid cells, B cells, in response to antigen, co-receptor stimulation and cytokines. Antibodies can bind to and inactivate antigen directly (neutralizing antibodies) or activate other cells of the immune system to destroy the antigen depending on isotype; IgM, IgG1, etc. Isotype class switching in B cells is controlled, inter alia, by cytokine milieu. Abnormalities in antigen response, co-receptor engagement or cytokine milieu can lead to suboptimal immune responses, tolerance or autoimmunity.

Cellular immune recognition is mediated by a special class of lymphoid cells, the T cells. These cells do not recognize whole antigens but instead respond to degraded peptide fragments thereof which appear on the surface of the antigen presenting cells bound to surface proteins called major histocompatibility complex (MHC) molecules. Two subgroups of T cells exist: the CD4 T cells recognize peptide fragments bound to MHC class II molecules while CD8 T cells recognize peptide fragments bound to MHC class I molecules. CD8 T cells include the population of cytotoxic T cells (CTL) able to specifically lyse antigen presenting cells. Essentially all nucleated cells have class I molecules. It is believed that proteins produced within the cell are continually degraded to peptides as part of normal cellular metabolism. These fragments are bound to the MHC molecules and are transported to the cell surface. Thus, the cellular immune system is constantly monitoring the spectra of proteins produced in all cells in the body and is poised to eliminate any cells producing foreign antigens or abnormal self antigens. CD4 T cells recognize mainly exogenous antigens that were taken up by antigen processing cells wherein the antigen is degraded and appears as a peptide fragment on class II MHC molecules. The effector function of CD4 cells is primarily regulation of immune responses by release of cytokines. According to the cytokine profiles secreted, two subclasses of CD4 cells have been defined, the TH1 and TH2 cells. It is believed that in various infections and allergic and autoimmune diseases the type of the CD4 T cell subclass activated (TH1 vs. TH2) critically influences the outcome of the immune response.

Vaccination is the process of preparing a human or an animal to respond to an antigen. Vaccination is more complex than immune recognition and involves not only B cells and cytotoxic T cells but other types of lymphoid cells as well. During vaccination, cells which recognize the antigen (B cells or T cells) are clonally expanded. In addition, the population of ancillary cells (helper T cells which provide co-receptor and cytokine stimulation) specific for the antigen also increase. Vaccination also involves specialized antigen presenting cells which can process the antigen and display it in a form which can stimulate one of the two pathways (macrophages and dendritic cells).

A foreign antigen is introduced into a human or an animal where it activates specific B cells by binding to surface immunoglobulins. It is also taken up by antigen processing cells, wherein it is degraded, and appears in fragments on the surface of these cells bound to Class II MHC molecules. Peptides bound to class II molecules are capable of stimulating the helper class of T cells (CD4 T cells). Both helper T cells and activated B cells are required to produce active humoral immunization. Cellular immunity is stimulated by a similar mechanism but entry into the MHC I presentation pathway of antigen presenting cells is typically by intracellular pathogen replication and not achieved by injection of protein antigen only.

Standard vaccination schemes nearly always produce a humoral immune response. The humoral system protects a vaccinated individual from subsequent challenge from a pathogen and can prevent the spread of an intracellular infection if the pathogen goes through an extracellular phase during its life cycle; however, it can do relatively little to eliminate intracellular pathogens. Cytotoxic immunity complements the humoral system by eliminating the infected cells and cancer cells. Thus, effective vaccination should advantageously activate both types of immunity.

A cytotoxic T cell response is necessary to remove intracellular pathogens such as viruses as well as malignant cells. It has proven difficult to present an exogenously administered antigen in adequate concentrations in conjunction with Class I molecules to assure an adequate response.

This has severely hindered the development of vaccines against tumor-specific antigens (e.g., on breast or colon cancer cells), and against weakly immunogenic viral proteins (e.g., HIV, Herpes, non-A, non-B hepatitis, CMV and EBV). It would be desirable to provide a cellular immune response alone in immunizing against agents such as viruses for which antibodies have been shown to enhance infectivity. It would also be useful to provide such a response against both chronic and latent viral infections and against malignant cells.

Directed and elevated immune responses to antigens can be achieved by the use of adjuvants and/or delivery vehicles. The term "immune adjuvant" refers to compounds which when administered to an individual or tested in vitro, increase the immune response to an antigen. Some antigens are weakly immunogenic when administered alone or are toxic at the concentration which evokes immune responses. An immune adjuvant may enhance the immune response of the individual to the antigen by making the antigen more immunogenic. The adjuvant effect may also lower the dose of antigen necessary to achieve an immune response by enhancing presentation, influence the cytokine milieu or alter co-receptor expression on antigen presenting cells.

Recently, it has been demonstrated that oligonucleotides and oligonucleotide derivatives may have a significant impact on certain biological processes. Thus, it has been shown that phosphorothioate oligonucleotides may have an influence on the regulation of gene expression [Bielinska et al., Science, vol. 250 (1990), p. 997–250]. Krieg et al. [Nature, vol. 374 (1995), p. 546–549] report that bacterial DNA may trigger direct B cell activation. They disclose that bacterial DNA and synthetic oligodeoxynucleotides containing unmethylated CpG dinucleotides induce murine B cells to proliferate and secrete immunoglobulin in vitro and in vivo. Yet, the system developed by Krieg et al. has not proven successful in every instance to trigger, modulate or enhance an immune response that is beneficial to the patient. In some instances, the system developed by Krieg even showed adverse effects. Thus, the technical problem underlying the present invention was to provide a means that is effectively and beneficially applicable in a wide variety of situations where stimulation, modulation or triggering of an immunological reaction is desired.

The solution to said technical problem is activated by providing the embodiments characterized in the claims.

Accordingly, the present invention relates to a pharmaceutical composition comprising at least one fragment of a polynucleotide and at least one antigen and, optionally, a pharmaceutically acceptable carrier and/or diluent.

The term "polynucleotide" in the sense of the present invention comprises all types of polynucleotides as well as derivatives thereof, e.g. RNA, PNA or DNA whereby, however, DNA polynucleotides are preferred. The term "fragment of a polynucleotide", as used in accordance with the present invention, may relate to a fragment generated from a polynucleotide or to a nucleic acid molecule that is shorter than a polynucleotide, such as an oligonucleotide which may be of synthetic origin.

The term "antigen" in the sense of the present invention means a molecule that can elicit an immune response. The immune response may be either humoral, i.e. antibody-mediated, or cellular, i.e. cell-mediated. An antigen that evokes an immune response is commonly referred to as immunogen. Generally only foreign or "non-self" molecules are immunogenic. It should be understood, however, that in the sense of the present invention, the term antigen comprises also certain "self" molecules such as tumor cells, tumor markers or self antigens in autoimmunity. Those compounds may not be foreign to the host to be treated, but may be comprised under the term antigen, since sometimes an immune response to self molecules is desired. In that case exogenous addition of antigen to the pharmaceutical composition may not be required. The fragment of the polynucleotide as well as the antigen may be of natural, synthetic or semisynthetic origin. Particularly, in the case that the antigen is of natural origin, it may be processed prior to administration.

Usually the larger and more complex a molecule is, the more immunogenic sites it will have. A single antigen may contain many epitopes which are specific areas of the molecule with a three-dimensional configuration that induces an immune response. Complex molecules, such as large proteins composed of many different amino acids contain more epitopes than a comparatively simple polysaccharide composed of two or three monosaccharide repeats. The immune response to a given antigen can vary greatly among species and individuals within a species due to immune regulation genes. The pharmaceutical compositions of the present invention comprise therefore specific polynucleotides which provoke a suitable immune response.

It is preferred that the fragment of the polynucleotide as used in the present invention comprises the sequence of a binding site for transcription factors or parts thereof or that the sequence of the polynucleotide is complementary to said binding site for transcription factors or a part thereof.

The expression of individual genes is a rather complex process. These processes are mediated by several specific regulatory DNA regions found in the promotor regions of almost all genes. These regulatory sequences are frequently referred to as response elements. They are binding sites for sequence-specific DNA binding proteins which are called transcription factors. Some transcription factors are general purpose factors (basal transcription factors) required for transcription of all genes while others act on specific genes or classes of genes by binding in a sequence-specific manner to response elements and other sequence motives within the corresponding gene promoters. The expression of many of these transcription factors is developmentally and also tissue-specifically controlled and is itself subject to the action of other transcription factors and other accessory proteins such as nuclear receptors. Binding sites for transcription factors are often clustered and a variety of transcription factors have been found to form complexes with others or to compete with others for binding to overlapping DNA-binding motifs. Several structural motifs have been found within those regions of transcription factor proteins recognizing and contacting DNA. Within each of these structural motifs there are often families of related proteins that recognize similar DNA sequences and are conserved throughout the eukaryotic kingdom.

In the course of the present invention it has been surprisingly found that bacterial sequences as described in the prior art may cause severe side effects such as lethal shock. It has been found, however, that other DNA sequences may have a beneficial effect on mammals and may therefore be used for the preparation of pharmaceutical compositions having a beneficial effect on the immune system. Thus, selection and identification of such beneficial DNA sequences may be effected on the basis of the teachings of the present invention.

The present invention also relates to a pharmaceutical composition comprising
(a) a polynucleotide or an oligonucleotide comprising the sequence of a binding site for transcription factors or a part thereof or a polynucleotide or an oligonucleotide comprising a sequence which is complementary to said binding site for transcription factors or a part thereof; and optionally (b) a pharmaceutically acceptable carrier and/or diluent.

In the course of the present invention it has been found that polynucleotides are preferred which have a sequence corresponding to the binding site of transcription factors or which are complementary thereto. Generally it is sufficient that at least a part of said binding site is contained within the polynucleotides. This embodiment of the invention is advantageously employed in conjunction with the above cited "self" molecules.

Advantageously, the pharmaceutical compositions of the present invention comprise inexpensive, stable and safe immune adjuvants and immunomodulatory substances for human and animal prophylactic and therapeutic use.

As has been stated above, the present invention relates to a pharmaceutical composition comprising at least one of the aforementioned regulatory sequences or antigens, either alone or in combination, and optionally a pharmaceutically acceptable carrier or excipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 $\mu$g to 10 mg units per day. If the regimen is a continuous infusion, it should also be in the range of 1 $\mu$g to 10 mg units per kilogram of body weight per minute, respectively. Progress can be monitored by periodic assessment. Dosages will vary but a preferred dosage for intravenous administration of DNA is from approximately $10^6$ to $10^{22}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery.

Advantageously, in the pharmaceutical compositions of the present invention liposomes can serve as carriers for the direction of antigen to antigen presenting cells. It has been demonstrated that liposomes can serve to heighten some humoral immune responses and to provide for exogeneously administered antigen a vehicle for entry into the MHC class I presentation pathway thus allowing the stimulation of cytotoxic T cells.

It is envisaged by the present invention that the various DNA oligonucleotides and/or polynucleotides or fragments thereof are administered either alone or in any combination using standard vectors and/or gene delivery systems, and optionally together with an appropriate compound, and/or together with a pharmaceutically acceptable carrier or excipient. Subsequent to administration, said DNA oligonucleotides and/or polynucleotides may be stably integrated into the genome of the mammal. On the other hand, viral vectors may be used which are specific for certain cells or tissues and persist therein. Suitable pharmaceutical carriers and excipients are well known in the art. The pharmaceutical compositions prepared according to the invention can be used for the prevention or treatment or delaying of different kinds of diseases, which are related to the expression or overexpression of genes.

Furthermore, it is possible to use a pharmaceutical composition of the invention which comprises DNA oligonucleotide in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy or antisense therapy may also be accomplished using a biolistic delivery system, such as that described by Williams (Proc. Natl. Acad. Sci. USA 88 (1991), 2726–2729).

Standard methods for transfecting cells with recombinant DNA are well known to those skilled in the art of molecular biology, see, e.g., WO 94/29469. Gene therapy and antisense therapy to diseases mentioned in accordance with the invention may be carried out by directly administering the DNA oligonucleotide to a patient or by transfecting cells with the DNA oligonucleotide ex vivo and infusing the transfected cells into the patient. Furthermore, research pertaining to gene transfer into cells of the germ line is one of the fastest growing fields in reproductive biology. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., WO94/29469, WO 97/00957 or Schaper (Current Opinion in Biotechnology 7 (1996), 635–640) and references cited therein. The DNA molecules and vectors comprised in the pharmaceutical composition of the invention may be designed for direct introduction or for introduction via liposomes, or viral vectors (e.g. adenoviral, retroviral) containing said recombinant DNA molecule into the cell. Preferably, said cell is a germ line cell, embryonic cell, or egg cell or derived therefrom. The pharmaceutical compositions according to the invention can be used for the treatment of diseases hitherto unknown as being related to susceptible to cytokine presence or concentration. An embryonic cell can be for example an embryonic stem cell as described in, e.g., Nagy, Proc. Natl. Acad. Sci. 90 (1993) 8424–8428.

In a preferred embodiment of the present invention the oligonucleotide or polynucleotide is a DNA oligonucleotide. DNA oligonucleotides as used in the present invention are preferably short fragments of a DNA having about 100, preferably five to about 40 and most preferably 15 to about 25 nucleotides.

The DNA polynucleotide fragments which are preferably oligomers provide when applied in relatively low quantities in the range of 0.1 to 10 $\mu$g the effect of an immune adjuvant and immunomodulatory substance together with low toxicity and low side effects. For example can a combination of a suitable DNA oligomer and tumor cells or specific tumor markers induce tumor regression. The invention also relates to corresponding uses.

In a preferred embodiment of the present invention the DNA oligonucleotide is single-stranded or double-stranded, whereby single-stranded DNA is especially preferred.

In a further preferred embodiment of the present invention, said sequences of binding sites for transcription factors are binding sites of transcription factors of cytokines.

In another preferred embodiment of the present invention, the polynucleotide contained in said pharmaceutical composition comprises the sequence 5'PuPuCGPyC or a non-toxic derivative thereof wherein Pu means purine and comprises adenine and guanine and Py has the meaning of pyrimidine and comprises cytosine, thymine and uracil and wherein A means adenine, C means cytosine and G means guanine.

Non-toxicity of said derivatives can be effected according to conventional protocols.

Those preferred sequences of the present invention differ slightly but biologically significantly from the CpG motifs as disclosed in the prior art.

It is furthermore preferred that in the pharmaceutical composition of the invention, said binding site is or is derived from a eukaryotic binding site.

The term "derived from" is intended to mean in accordance with this invention that one or more nucleotides from a naturally occurring binding site are changed. Said change can be effected according to conventional protocols such as mutagenesis protocols.

It is particularly preferred that said eukaryotic binding site is a binding site for a cytokine.

As regards the part of said binding site for said transcription factor or its complementary sequence, it is preferred that said part is a motif or a complementary sequence thereof. Motifs of transcription factors are well known in the art and need not be discussed here any further.

It is furthermore particularly advantageous that said part comprises at least 7 nucleotides. Whereas this length of said part (and, of course, of the complete oligonucleotide as well) has been particularly advantageous, it may also comprise significantly more than 7 nucleotides.

It is preferred that the polynucleotide comprises at least one phosphorothioate linkage. In the preferred phosphorothioate derivatives of the polynucleotides at least one oxygen atom of the phosphate backbone of the polynucleotide is replaced by a sulphur atom. Those compounds are more stable against degradation.

It is also possible to add to the pharmaceutical composition of the present invention further classical adjuvants which are known to the person skilled in the art. Examples may be preparations from the cell walls of bacteria. The pharmaceutical compositions of the present invention advantageously comprise also additives, otherwise known as pharmaceutically acceptable carriers and/or diluents known to the person skilled in the art depending on the administrative way e.g. oral, parenteral or rectal.

It is possible to use in accordance with the present invention a wide variety of antigens. Preferred antigens are selected from the group comprising peptides, polypeptides, steroides and tumor cells.

Further examples for preferred antigens may be killed intact bacteria, toxoides (i.e. toxines that are still immunogenic but are rendered biologically inactive by treatment with a chemical, heat or mutation), subunit vaccines in which only the non-toxic portion of the molecule is used or life-attenuated vaccines in which a viral or bacterial strain is rendered non-pathogenic (e.g. by passaging the virus in cell culture or deletion of bacterial genes), but is still able to multiply to a limited degree thereby eliciting protective immune response in the absence of disease symptoms.

Since the pharmaceutical composition of the present invention can also be used for the treatment and/or prophylaxis of such diseases which are not caused by foreign organisms the antigen may be also an antigen of the own body like a tumor antigen. For the treatment of autoimmune diseases or in order to positively influence the tolerance it may also be effective to use antigens derived from the body to be treated. In that cases it may not be required to add the antigen to the pharmaceutical composition since the antigen is already present in the host.

In the accomplishment of the foregoing objectives of the invention, vaccine formulations are made which induce both humoral and cellular immune responses to antigen using preferably sequences with non-toxic embodiments of the motif 5'Pu-Pu-CpG-Py-Py-3'. Some sequences, especially with the motif 5'Pu-Pu-CpG-Py-Py-3' can be toxic and lethal. It is therefore another aspect of the invention to modify these sequences in such a way that immune adjuvant activity is maintained but toxicity is eliminated. In addition, DNA sequences are described which do not follow this motif but serve as immune adjuvant and immune response modifiers. A common aspect of the invention is that sequences from eukaryotic promoters are used. ssDNA sequences containing palindromic and non-palindromic transcription response elements, that is sequences recognized by transcription factors (proteins which regulate gene transcription) serve also as immune adjuvant or immune response modifiers in accordance with the invention. These sequences are capable of modulating lymphocyte cell surface markers and cytokine release in vitro and in vivo. In yet another aspect of the invention, the methods of treatment are pharmaceutical compositions and appropriate utilized therapeutic approaches for treating immune system tolerance and control of tumor.

The teaching of the present invention can be used for modulating the immune response to antigen by using certain DNA oligomers. The particular DNA depends on the desired outcome. Its sequence can be determined by the person skilled in the art without further ado on the basis of the teachings of the present invention. The invention works in vitro and in vivo in warm blooded animals.

A common aspect of the invention is to use the polynucleotide fragment and, in particular, certain DNA oligonucleotides to specifically influence the regulation and signalling machinery of eukaryotic cells. In particular, growth, induction of cellular transcription and translation, protein synthesis or protein secretion can be modified by DNA oligonucleotides. In addition, response patterns of eukaryotic cells towards exogenous stimuli are subject of modification. Modification of the response the eukaryotic cell is controlled by the sequence of the oligonucleotide, i.e. is sequence-specific. The invention gives a rule how active DNA oligonucleotides can be selected. For example, by simply modifying known transcription factor binding sites, e.g., by mutagenesis techniques and testing the modified sequences by, for example, conventional protocols or protocols described in this specification, said active oligonucleotides can be identified. Accordingly, active DNA oligonucleotides are derived from DNA-sequences able to be bound by transcription factors. These sequences can be identified from eukaryotic promoters.

The invention concerns also the use of specific oligonucleotides or polynucleotide fragments as defined herein above which are preferably DNA for the preparation of a pharmaceutical composition which have the effect to interfere, to modulate and to regulate responses of the innate and acquired immune system. Those include enhancement of immune responses (including vaccination), modulation of immune responses and suppression of immune responses.

Use of DNA oligomeres to enhance the reactivity of immune cells to viral, bacterial and parasitic antigens is another object of the invention. Enhancement includes induction of immunological memory, cytotoxic T cells, cytokine release and augmentation of innate immunity (phagocytosis, cytokine release and cytolytic function). In particular, DNA oligomers can be used as an adjuvant for T- and B-cell vaccination. Enhancement further includes induction of reactivity against weak or tumor antigens. The use of DNA oligonucleotides to break tolerance in anergic T and B cells e.g. against tumor antigens is a further object of the invention. This incorporates the use of DNA oligonucleotides as adjuvants in vaccination against tumor-defined antigens and immunostimulatory substances in an ongoing immune response against tumors.

Use of DNA oligos to modulate responses of the acquired immune system is also an aspect of the present invention. Desired immune responses can be stimulated while adverse effects can be suppressed by DNA oligonucleotides. DNA oligonucleotides can shift an immune response to a TH1-type or a TH2-type of reactivity. This effect modulates the response during parasitic infections (Leishmaniasis, Toxoplasmosis, or Mycobacteriosis). In addition, the use of DNA oligonucleotides to direct a B cell immune response towards certain classes of immunoglobulins, thus bypassing and overcoming the adverse Ig-dependent diseases like Ig-E-mediated allergy is also an aspect of the present invention.

Use of DNA oligos to suppress immune reactions of the innate and acquired immune system is also an aspect of the present invention. DNA oligonucleotides can be used to suppress B- and T-cell responses towards transplantation antigens and thus induce transplantation tolerance. DNA oligonucleotides can further be used to suppress ongoing or manifested immune responses as it is the case during T- and B-cell dependent autoimmune diseases.

The pharmaceutical preparations of the present invention preferably comprise polynucleotides applied together with antigen either in free form or entrapped in liposomes. The science of forming liposomes is now well developed. Liposomes are unilamellar or multilamellar vesicles having a membrane portion formed of lipophilic material and an interior aqueous portion. The aqueous portion is used in the present invention to contain the antigen and, probably, protein material to be delivered to the antigen presenting cell. Conventional methods can be used to prepare liposomes. They are taken up by macrophages and dendritic cells in vivo and are thus particularly effective for delivery of antigen to these cells.

Liposomes may be manufactured by a rehydration entrapment method. Preferably the liposomes are prepared as follows. 18.0 mg phosphatidylcholine; 2.0 mg phosphatidylglycerol and 5.0 mg cholesterol, at a 2:0.2:1 ratio, are suspended in 5.0 ml chloroform in a 100 ml round bottom flask. The mixture is rotary evaporated under reduced pressure until a thin lipid film forms on the flask wall. Residual chloroform is removed by vacuum desiccation. 3 mg of ovalbumin is solubilized in 1.0 ml of PBS.

This solution is slowly added to the dried lipid and hand-shaken until the lipids are resuspended. The crude protein liposome mixture is allowed to equilibrate for 30 min at room temperature, transferred to a microfuge tube and centrifuged at 6,000 rpm for 5 min in an Eppendorf microfuge. The mixture is then filter-extruded through a 0.2 $\mu$g Anotop10® syringe mount filter. To this mixture 10 nmol oligomer is added per 100 $\mu$l.

The pharmaceutical composition of the invention may advantageously be tested in mice. In such experiments mice were usually immunized by way of the hind footpad with 50 $\mu$l per foot of peptide liposome preparation. After four days, the draining popliteal lymph nodes (LN) were removed and a single-cell suspension was prepared. The cells were cultured for four days in the presence of IL-2 and a chromium release assay was performed utilizing the syngenic target cell EL-4 or the cell line EG-7 which is transfected with the gene for ovalbumin and thus presents ovalbumin peptides as antigen (FIG. 1). In some experiments EL-4 pulsed with the MHC class I ($K^b$) restricted ovalbumin peptide SIINFEKL (SEQ ID NO: 3) was used as the target for kill.

The present invention also comprises methods of immunizing patients against a variety of diseases and conditions that have been referred to herein above or of treating patients suffering from one of the above referenced conditions or diseases. Formulations, routes of administration and doses have been identified herein above in connection with the discussion of the pharmaceutical compositions of the invention.

Finally, the invention relates to a method comprising
(a) testing a nucleic acid molecule comprising a putative binding site of a transcription factor for toxicity;
(b) modifying the nucleic acid sequence of said putative binding site comprised in said nucleic acid molecule which has proven toxic in step (a); and
(c) repeating steps (a) and (b) one or more times until a non-toxic nucleic acid molecule has been identified.

Isolation of nucleic acid molecules to be tested, testing procedures as well as modification procedures for the nucleic acid sequences are well known in the art and had been described in the present specification, respectively.

An oligonucleotide that has been identified to be beneficial in accordance with the invention is IL-12p40 AGCTA TGACGTTCCAAGG (SEQ ID NO:10).

The figures show:

FIG. 1: Cytolytic T cell induction in vivo with different ssDNA adjuvants.

Mice were injected with the antigen ovalbumin entrapped in liposomes using the indicated adjuvant. T cells were harvested from the mice and tested for the specific recognition of the antigen. The assay indicated a strong activation of the cellular immune system due to the adjuvant. AP-1, Stat-5/6, SIE, c/Myb, Stat3, Stat4, Stat5, SP-1, C/EBP, IL-13, Stat1, CRE, Erg and IRF-1 are binding sites for transcription factors.

Figure 2:
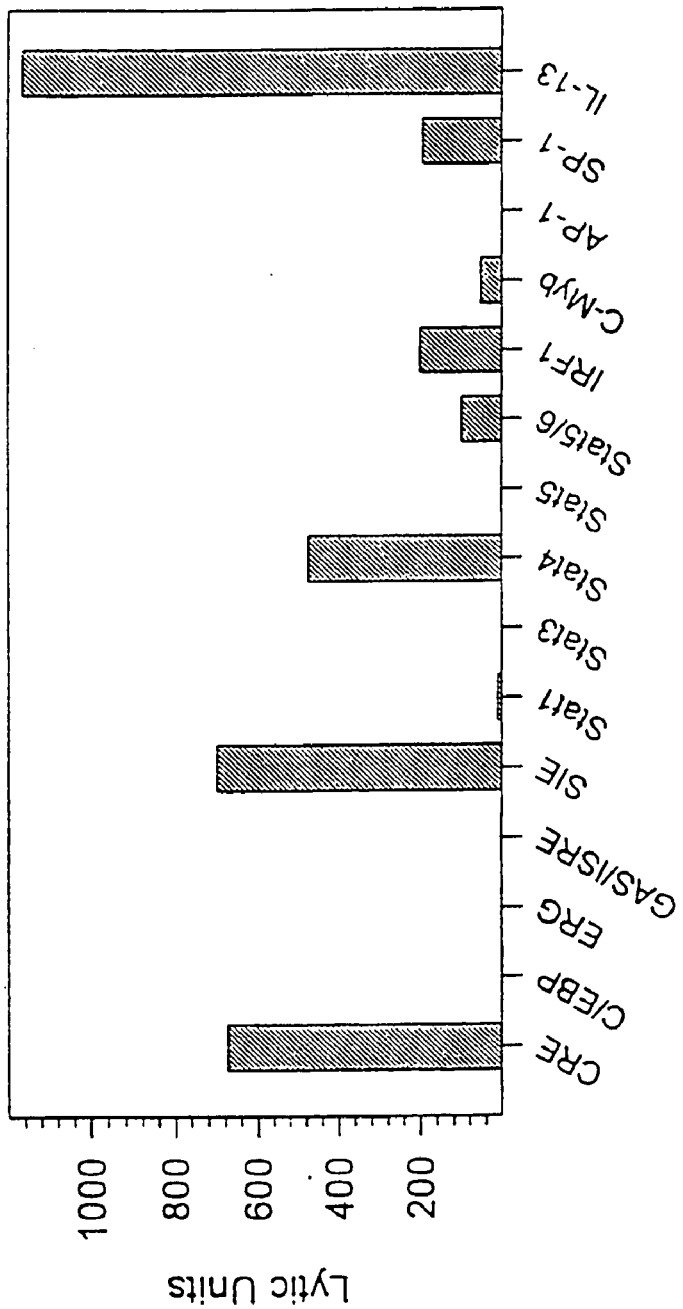

FIG. 2: A summary of cytolytic T cell assay.

Different sequences were tested. In vivo induced CTL were tested for specific antigen recognition. Data are expressed as lytic units.

A lytic unit is arbitrarily defined as the number of lymphocytes required to yield 30% specific lysis. The number is the lytic units per $10^6$ effector cells. Lytic units are a way to compare cytolytic T cell populations.

Figure 3:
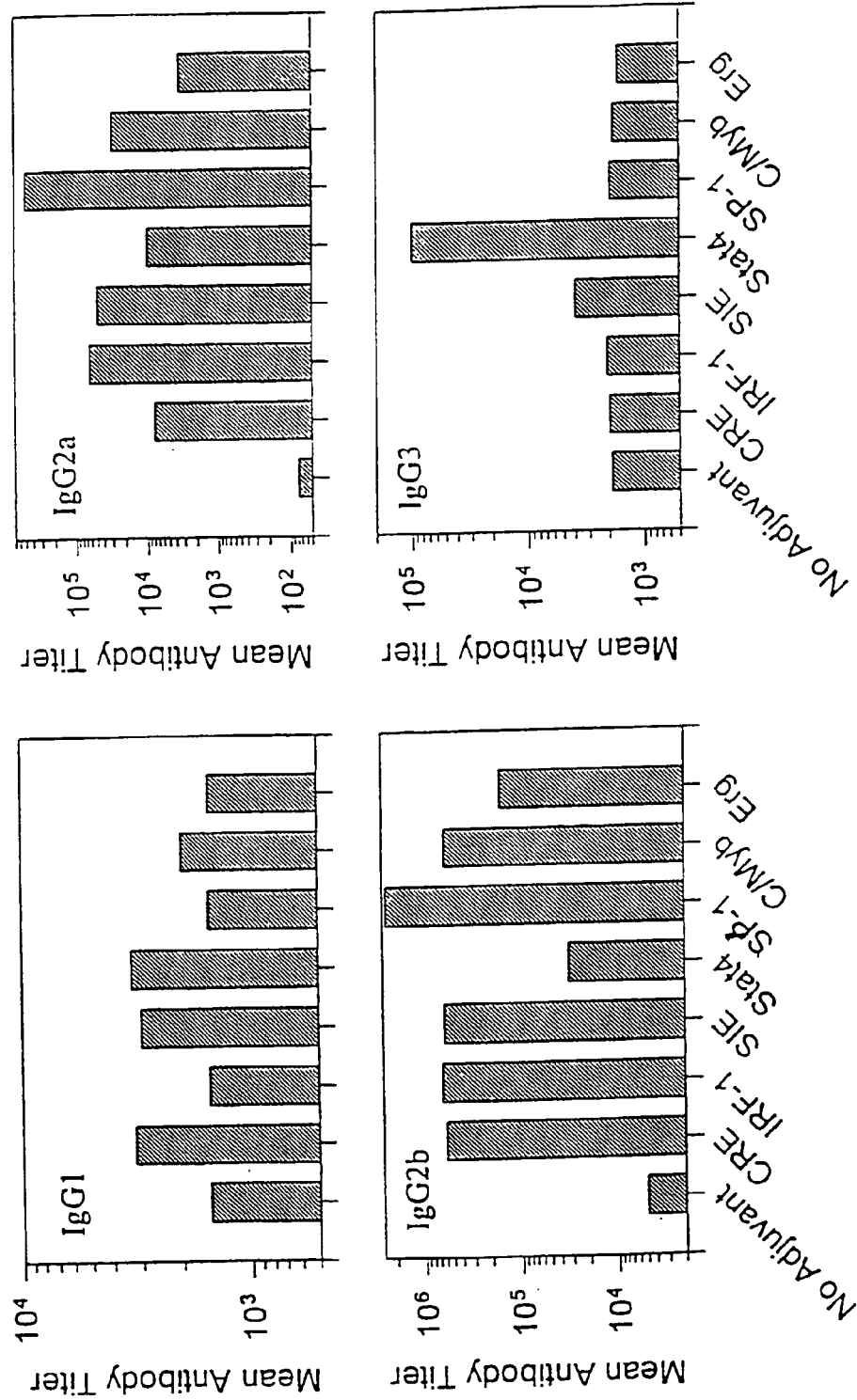

FIG. 3: Antibody production by ssDNA adjuvants post injection.

Endpoint antibody titer assay: Mice were injected with the antigen ovalbumin entrapped in liposomes using either no adjuvant or a TRE (transcription regulatory elements) adjuvant. The mice were boosted once.

The assay indicates a strong adjuvant effect for the enhancement of antibody production in response to injected antigen. The adjuvant-assisted increase in response is particularly strong for IgG2a and IgG2b. Of note is the differential induction of antibody isotype dependent on the adjuvant used indicating differential cytokine release.

Figure 4:
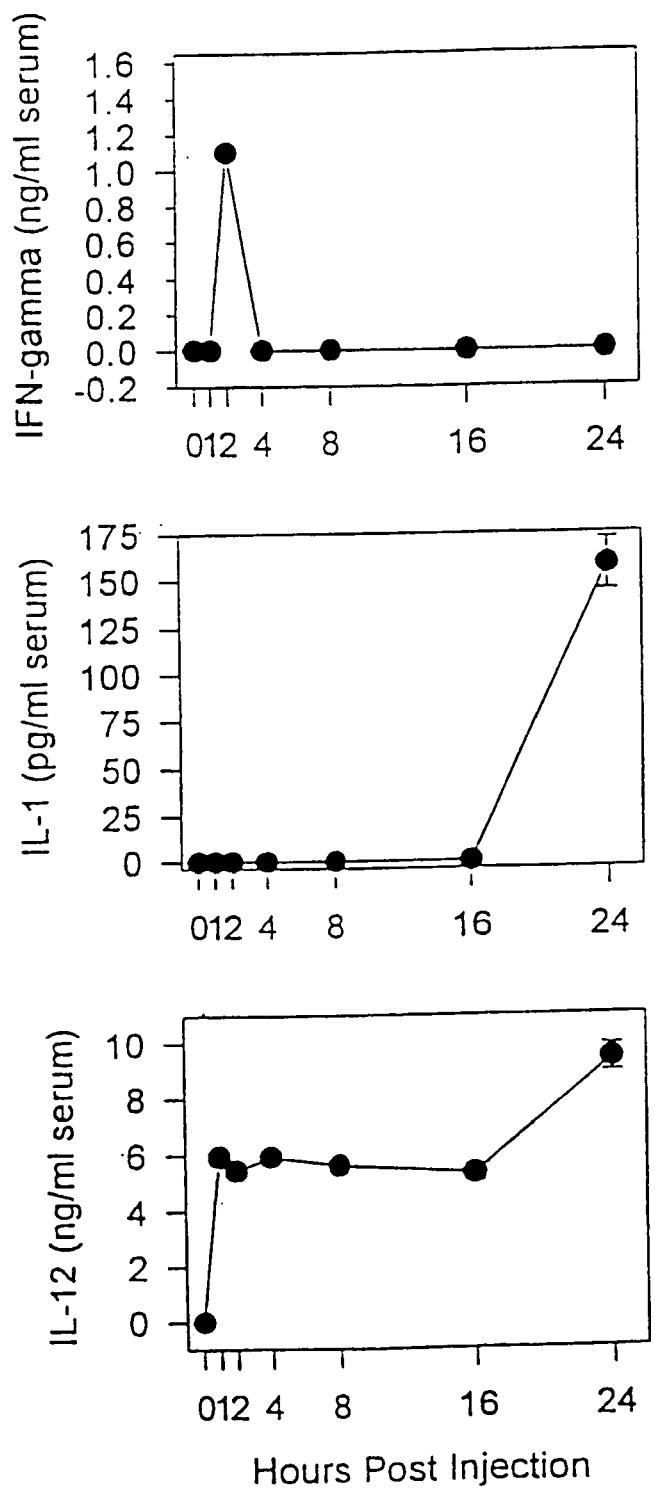

FIG. 4: Cytokine induction in vivo with transcription response element ssDNA adjuvant CRE.

The cytokine release pattern is induced by the transcription response element CRE. Mice were injected with the ssDNA and at the indicated time serum was sampled and cytokine release measured.

Figure 5:
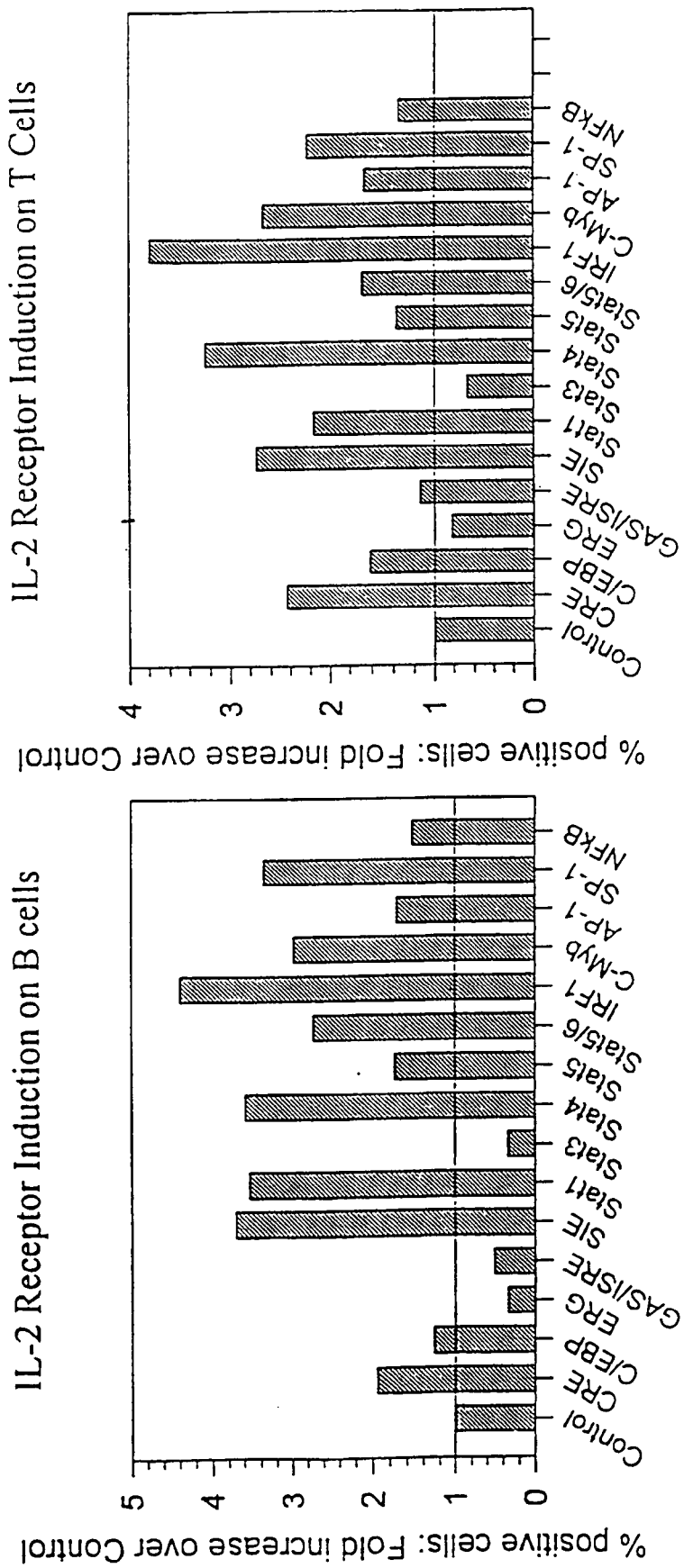

FIG. 5: Phenotype changes (IL-2 receptor expression) of B and T cells in vivo with different transcription response element ssDNA adjuvants.

Analysis of a relevant cell surface marker after treatment with ssDNA. The IL-2 receptor binds and transduces a proliferation signal from IL-2 to cells of the immune system. The TRE sequences vary in their T stimulation capacity for inducing IL-2 receptor expression. Some TRE are inhibitory indicating a potential use for negative immunmodulation.

Figure 6:
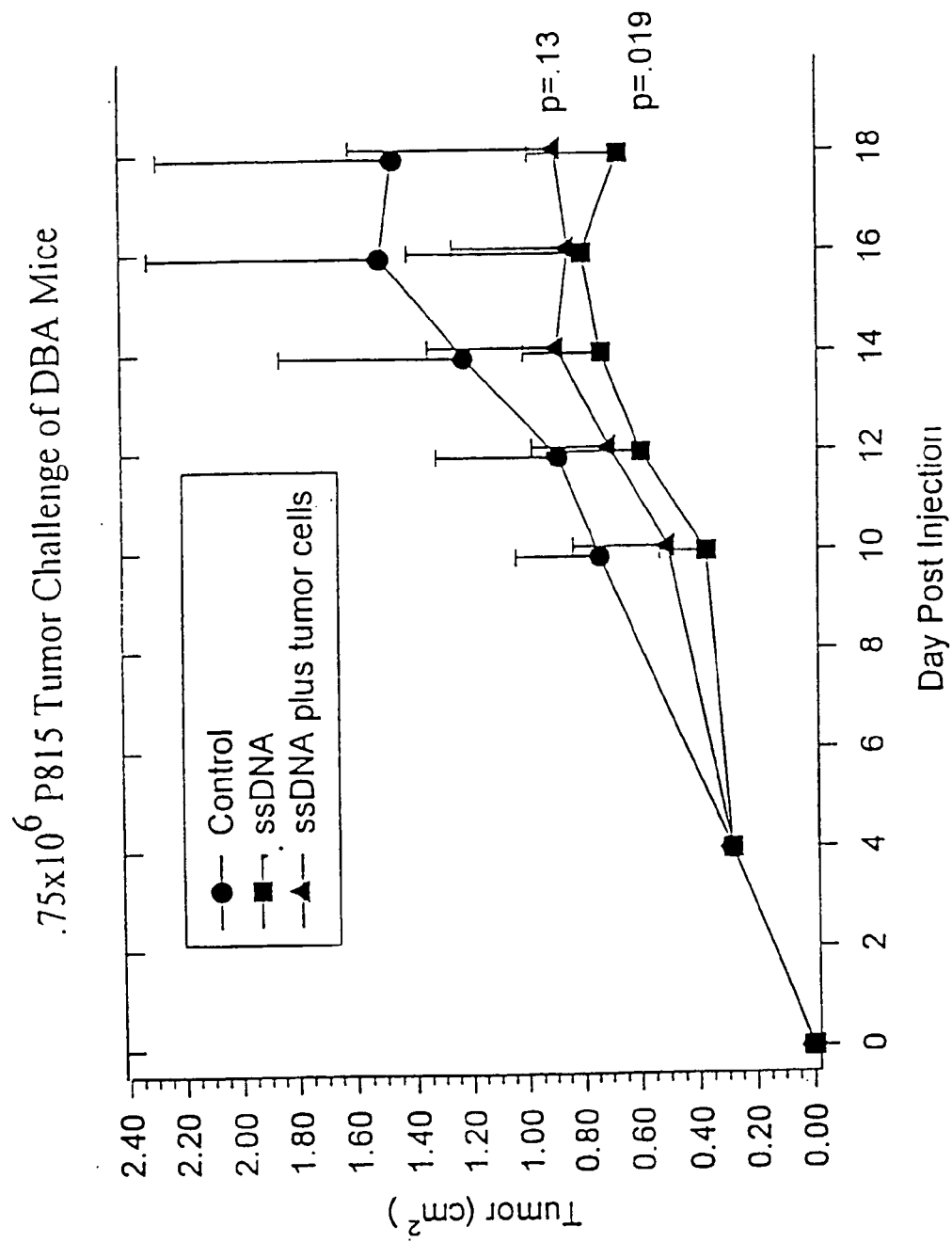

FIG. 6: Tumor regression and control with ssDNA. ssDNA induces regression of preexisted tumor.

Mice were injected with tumorigenic numbers of a syngenic tumor cell. Four days after the challenge the mice were treated with ssDNA alone or ssDNA plus a subtumorigenic number of tumor cells, which served as an antigen source. The progression of tumor growth was significantly controlled. Five mice were included per group.

Figure 7:
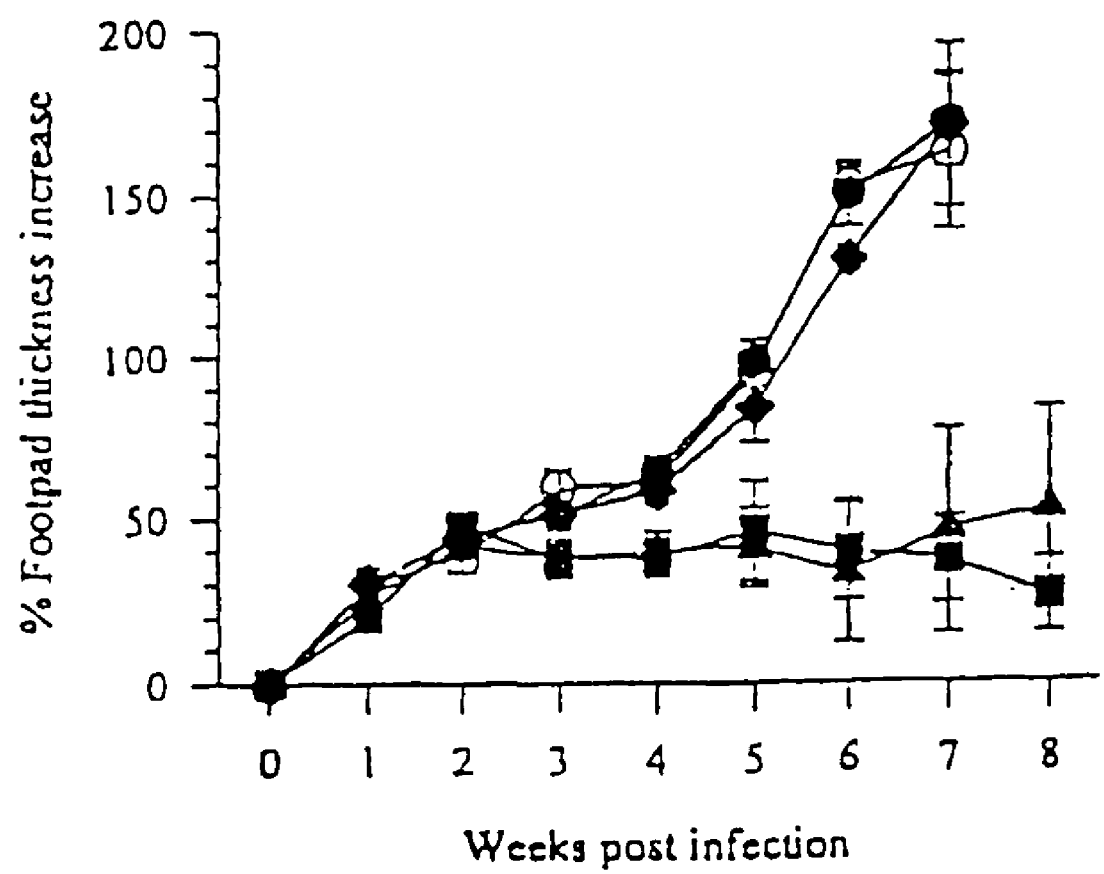

FIG. 7: Course of infection with L. major in ODN-treated mice.

BALB/c mice were injected with 2×10$^6$ L. major promastigotes into the right hind footpad. Oligonucleotide (ODN) (10 nmol) was given as treatment 2 h before and 10 h after infection. The mean percent increase (±SD of the footpad thickness is given (three mice per group). Closed symbols indicate the ODN-treated groups and the open circle the non-ODN-treated control group. ODN treatments are: closed circle, 1720; closed diamond, AP-1; closed triangle, 1668; closed square; IL-12-p40.

The examples illustrate the invention.

EXAMPLE 1

Bacterially derived sequences can be used as an adjuvant for cytolytic T cell activation in vivo.

Three sequences containing the sequence motif of 5'Pu-Pu-CpG-Py-Py-3' are described in the literature for having immunostimulating properties. One sequence is derived from the ampicillin resistance gene of E. coli, here termed AMP (TCATTGGAAAACGTTCTTCGGGGC; SEQ ID NO: 1). The second sequence is derived from a BCG gene and is termed BCG-A4A (ACCGATGACGTCGCCGGT-GACGGCACCACG; SEQ ID NO: 2). The third is a synthetic sequence claimed to be a prototype of bacterial CpG sequences, referred to by Krieg et al. as 1668 (TCCAT GACGTTCCTGATGCT; SEQ ID NO: 4). These sequences were synthesized to include a phosphorothioate linkage to reduce destruction by DNase. These oligomers served as an adjuvant in combination with ovalbumin to induce a cytolytic T cell response.

EXAMPLE 2

Bacterial CpG containing sequences may be toxic.

We observed that the above-described oligomers could be highly toxic in vivo for mice sensitive to TNF-α. The 1668 oligomer was previously described by Krieg and co-workers for its ability to induce murine B cell proliferation, induce IL-6 release from B cells and induce IFN-γ release from B cells and induce IFN-γ release from NK1.1 cells. We found in addition that 1668 and AMP were highly lethal in mice sensitized to the effects of TNF-α (Table 1). However, under certain circumstances these sequences may be useful therapeutically. One could foresee the use of these sequences once the risk is properly assessed.

TABLE 1

| Death due to lethal shock | |
|---|---|
| 1668 + D-gal | 5/5 |
| 1668 + LPS | 3/3 |
| AMP + LPS | 2/3 |
| Control | 0/3 |

Ratio=mice killed/mice injected

For lethal shock, Balb/c mice were injected intraperitoneally with 10 nmol 1668 in 200 μl PBS plus 20 mg D-galactosamine in 200 μl PBS. Alternatively mice were injected intravenously with 10 nmol 1668, AMP or PBS followed at four hours with 50 μg LPS.

EXAMPLE 3

Use of eukaryotic transcription regulatory elements or sequence manipulation prevents toxic shock symptoms.

Due to toxicity, the need is established for the discovery of non-toxic sequences for safe human and animal use. Since toxicity is at issue when developing vaccine adjuvants and therapeutics, we were interested to develop oligomers that circumvented toxicity but retained immunostimulatory properties. We screened eukaryotic sequences displaying the absence of lethality but maintaining immunostimulatory qualities. One such sequence was the cyclic AMP response element (CRE) which is the consensus binding site for the transcription factors CREB/ATF as well as the AP-1 family, sequence (GATTGCCTGACGTCAGAGAG; SEQ ID NO: 8) [Roesler, W. J. et al., J. Biol. Chem. 263, 9063–9066 (1988)]. Table 2 demonstrates the loss of lethality of the CRE sequence. To further evaluate the sequence specificity of these effects we made sequence exchanges between CRE and 1668. An exchange of only two nucleotides between CRE and 1668 resulted in a loss of lethality (Table 2).

EXAMPLE 4 ssDNA containing transcription response elements (TRE) serve as adjuvant for antibody production.

In accordance with the invention, eukaryotic transcription response elements relevant to the immune system serve as immune adjuvant. To test the adjuvant qualities of different sequences we injected mice with either free ovalbumin plus oligomer or liposome encapsulated ovalbumin plus oligomer. The mice were boosted at day 14 and after one week ovalbumin specific endpoint antibody titers were determined in an isotype specific ELISA.

FIG. 3 shows that different sequences strongly potentiated the antibody response and induced class switching toward IgG1, IgG2a and IgG2b.

Liposomes containing ovalbumin were prepared as described above. For antibody induction, 300 μg ovalbumin in PBS or liposomes containing ovalbumin were injected +/−10 nmol oligomer in the hind footpads of C57/B6 mice. A boost of the like inoculum was given after two weeks and one week later blood was extracted for serum antibody titering.

EXAMPLE 5 ssDNA containing transcription response elements serve as adjuvant for cellular immunity.

We have described the use of liposomes in combination with Quil A or QS-21 to induce cytolytic T cells (CTL) to either soluble antigen or peptides [Lipford, G. B., Wagner, H. & Heeg, K., Vaccine 12, 73–80 (1994), Lipford, G. B. et al., J. Immunol. 150, 1212–1222 (1993)]. Liposome entrapped antigen alone was an ineffective inducer of CTL activity, but with the addition of immunostimulatory saponins the inoculum became effective. To test the in vivo T cell immunomodulatory potential of oligomers we utilized this vehicle to demonstrate primary activation of CTL. FIG. 1 shows a substantial primary CTL response induced by an inoculum of ovalbumin liposomes plus ssDNA matching transcription response elements. The lytic units value interpolated from these curves was approximately 500 L.U. as compared to <20 L.U. for ovalbumin liposomes only (Table 3). CTL memory, an important quality for vaccine protection, could also be demonstrated with these inocula. If mice were rested for two weeks after the first injection and reinjected with the same inoculum, CRE recalled CTL displaying lytic units measured at approximately 1500 L.U. (Table 3). Additional, when the inoculum was formulated with the immunodominant $K^b$ restricted ovalbumin peptide SIINFEKL (SEQ ID NO: 3), the oligomers induced a specific primary CTL response. Thus, oligomers serve as a strong in vivo stimulus resulting in T cell activation and the proliferation of antigen specific CTL effectors. The inoculum can contain protein or peptide as the target antigen.

TABLE 3

Cytolytic T cell response induced by oligomer in lytic units

|  | CRE | PBS |
| --- | --- | --- |
| Primary CTL | 526 L.U. | <20 L.U. |
| Secondary CTL | 1555 L.U. | <20 L.U. |

Several other sequences have been determined to have immunomodulatory effects. Table 4 lists tested eukaryotic transcription response elements (TRE), which are preferably used in the present invention.

TABLE 4

Sequence of ukary tic TRE te t d

| | | |
| --- | --- | --- |
| CRE | GATTGCCTGACGTCAGAGAG | (SEQ ID NO: 8) |
| IL-13 | GGAATGACGTTCCCTGTG | (SEQ ID NO: 9) |
| AP-1 | GCTTGATGACTCAGCCGGAA | (SEQ ID NO: 11) |
| SP1 | TCGATCGGGGCGGGGCGAGC | (SEQ ID NO: 12) |
| C/EBP | TGCAGATTGCGCAATCTGCA | (SEQ ID NO: 13) |
| ERG | AGCGGGGGCGAGCGGGGGCG | (SEQ ID NO: 14) |
| GAS/ISRE | TACTTTCAGTTTCATATTACTCTA | (SEQ ID NO: 15) |
| SIE | GTCCATTTCCCGTAAATCTT | (SEQ ID NO: 16) |
| STAT1 | TATGCATATTCCTGTAAGTG | (SEQ ID NO: 17) |
| STAT3 | GATCCTTCTGGGAATTCCTA | (SEQ ID NO: 18) |
| STAT4 | CTGATTTCCCCGAAATGATG | (SEQ ID NO: 19) |
| STAT5 | AGATTTCTAGGAATTCAATC | (SEQ ID NO: 20) |
| STAT5/6 | GTATTTCCCAGAAAAGGAAC | (SEQ ID NO: 21) |
| IRF-1 | AAGCGAAAATGAAATTGACT | (SEQ ID NO: 22) |
| c-Myb | CAGGCATAACGGTTCCGTAG | (SEQ ID NO: 23) |
| NFkB | ATATAGGGGAAATTTCCAGC | (SEQ ID NO: 24) |
| HSINF | CAAAAAAATTTCCAGTCCTT | (SEQ ID NO: 25) |
| HSIL-6 | ATGTTTTCCTGCGTTGCCAG | (SEQ ID NO: 26) |
| CRENFkB | CTCTGACGTCAGGGGAAATTTCCAGC | (SEQ ID NO: 27) |

The relative strength of the various transcription response elements for adjuvant potential for CTL induction can be seen in FIG. 2.

EXAMPLE 6 ssDNA containing transcription response elements induce cytokine release in vivo.

Mice were injected with formulations containing different oligomers plus liposome or liposomes containing 300 μg ovalbumin. Serum was collected at various times and analyzed for serum cytokine levels by specific ELISA.

In addition T cells produce IL-2 in response to ssDNA. It was found that cytokine release patterns are sequence dependent and thus the eukaryotic transcription response element used influences the cytokine release outcome and thus the biological effects. This aspect of the invention is highly relevant, because cytokine release patterns can be influenced by different transcription response elements. ssDNA can be used to induce cytokine release in vivo to produce a desired outcome. This outcome could be to produce immune enhancement or immune suppression.

ssDNA containing transcription response elements can break tolerance in T cells. It can be demonstrated that T cells induced to become tolerant (that is non-response to antigen signals) in vivo by SEB injection break tolerance if ssDNA is injected up to seven days post tolerance induction. This finding has relevance for the development of specific modulations for desired biological outcome. It can be foreseen that ssDNA can be used to elevate the immune response of immunocompromised patients.

EXAMPLE 7a ssDNA containing transcription response elements induce co-receptor and surface receptor change on B and T cells. This finding has relevance for the development of specific modulations for desired biological outcome.

Mouse spleen cells were harvested and cultured 24 hours in the presence of the list eukaryotic TRE. Cell surface markers were measured on T or B cell by FACS analysis.

Some of the transcription response elements have a positive effect and some have a negative effect. Both types of results are of potential medical use. If immune enhancement is desired a sequence inducing a given cell surface marker would be of use. If immune suppression is desired a sequence suppressing a given cell surface marker would be of use. Further guidance on such selection is provided in Example 7b.

EXAMPLE 7b ssDNA containing transcription response elements induce (a) expression of co-stimulatory molecules B7.1, B7.2 and CD40, (b) production of the cytokine IL-12, IL-6 and TNF-α on murine dendritic cells. These events (termed maturation and activation) are associated with the acquisition of professional antigen presenting activity to naive T cells.

Immature murine dendritic cells were grown from bone marrow cells in GM-CSF conditioned medium according to published protocols. At day 8 to 11 of culture, non-adherent cells were either MHC class II negative, or intermediate (termed immature DC) or high (termed mature DC). FACS® sorting of MHC class II intermediate or high cells revealed DC-like morphology. Bacterial DNA or ssDNA containing transcription response elements strongly upregulated CD80 (B7.1) CD86 (B7.2) CD40 and MHC class II molecules on immature DC, as measured by FACS analysis. In addition, i.s. (immune stimulating) DNA containing transcription response element triggered production of high concentrations of IL-12, TNF-α and IL-6. Finally, the i.s. DNA matured/activated DC (derived from sorted MHC class II intermediate cells) expressed professional APC function as assayed in an allogenic "mixed lymphocyte reaction" and in primary T cell cultures stimulated with the superantigen "staphylococcal enterotoxin B" (SEB). It is known that SEB does not require processing but requires professional APC for presentation to naive Vβ8 T cells. Conversion, as induced by ssDNA, of immature DC into professional APC explains the powerful adjuvant effect of ssDNA containing transcription response elements in in vivo on humoral and T cell response to poorly immunogenic antigens used for vaccination.

EXAMPLE 8 ssDNA containing transcription response elements can induce tumor control or regression.

FIG. 6 demonstrates that mice challenged with tumor cells progress rapidly to display measurable subcutaneous tumors. These tumors are lethal. If ssDNA is injected four days post challenge the tumor regress or show retarded rates of growth. In addition if cells are provided as antigen the same observation is made.

EXAMPLE 9

Course of infection with L. major in ODN-treated mice.

BALB/c mice were injected with $2 \times 10^6$ L. major promastigotes into the right hind footpad. Oligonucleotide (ODN) (10 nmol) was given as treatment 2 h before and 10 h after infection. The mean percent increase (±SD of the footpad thickness is given (three mice per group). Closed symbols indicate the ODN-treated groups and the open circle the non-ODN-treated control group. ODN treatments are: closed circle, 1720; closed diamond, AP-1; closed triangle, 1668; closed square; IL-12-p40.

The invention claimed is:

1. A pharmaceutical composition, comprising:
   (a) at least one polynucleotide of a length of 100 nucleotides or less, wherein the polynucleotide comprises a sequence of a binding site for a transcription factor and which is selected from the group consisting of GATTGCCTGACGTCAGAGAG (SEQ ID NO:8),
   GGAATGACGTTCCCTGTG (SEQ ID NO:9),
   AGCTATGACGTTCCAAGG (SEQ ID NO:10),
   GCTTGATGACTCAGCCGGAA (SEQ ID NO:11),
   TCGATCGGGCGGGGCGAGC (SEQ ID NO:12),
   TGCAGATTGCGCAATCTGCA (SEQ ID NO:13),
   AGCGGGGCGAGCGGGGCG (SEQ ID NO:14),
   GTCCATTTCCCGTAAATCTT (SEQ ID NO:16),
   TATGCATATTCCTGTAAGTG (SEQ ID NO:17),
   CTGATTTCCCCGAAATGATG (SEQ ID NO:19),
   AGATTTCTAGGAATTCAATC (SEQ ID NO:20),
   GTATTTCCCAGAAAAGGAAC (SEQ ID NO:21),
   AAGCGAAAATGAAATTGACT (SEQ ID NO:22), and
   CAGGCATAACGGTTCCGTAG (SEQ ID NO:23);

(b) at least one antigen; and
   (c) a pharmaceutically acceptable carrier and/or diluent.

2. The pharmaceutical composition according to claim 1 characterized in that the polynucleotide comprises at least one phosphorothioate linkage.

3. The pharmaceutical composition according to claim 1, wherein the antigen is selected from the group consisting of peptides, polypeptides, proteins, polysaccharides, steroids, tumor cell antigens, and tumor cells.

4. The pharmaceutical composition according to claim 1, wherein the polynucleotide comprises a sequence GATTGCCTGACGTCAGAGAG (SEQ ID NO:8).

5. The pharmaceutical composition according to claim 1, wherein the polynucleotide comprises a sequence GGAATGACGTTCCCTGTG (SEQ ID NO:9).

6. The pharmaceutical composition according to claim 1, wherein the polynucleotide comprises a sequence AGCTATGACGTTCCAAGG (SEQ ID NO:10).

7. The pharmaceutical composition according to claim 1, wherein the polynucleotide comprises a sequence GCTTGATGACTCAGCCGGAA (SEQ ID NO:11).

8. The pharmaceutical composition according to claim 1, wherein the polynucleotide comprises a sequence TCGATCGGGGCGGGGCGAGC (SEQ ID NO:12).

9. The pharmaceutical composition according to claim 1, wherein the polynucleotide comprises a sequence TGCAGATTGCGCAATCTGCA (SEQ ID NO:13).

10. The pharmaceutical composition according to claim 1, wherein the polynucleotide comprises a sequence AGCGGGGGCGAGCGGGGGCG (SEQ ID NO:14).

11. The pharmaceutical composition according to claim 1, wherein the polynucleotide comprises a sequence GTCCATTTCCCGTAAATCTT (SEQ ID NO:16).

12. The pharmaceutical composition according to claim 1, wherein the polynucleotide comprises a sequence TATGCATATTCCTGTAAGTG (SEQ ID NO:17).

13. The pharmaceutical composition according to claim 1, wherein the polynucleotide comprises a sequence CTGATTTCCCCGAAATGATG (SEQ ID NO:19).

14. The pharmaceutical composition according to claim 1, wherein the polynucleotide comprises a sequence AGATTTCTAGGAATTCAATC (SEQ ID NO:20).

15. The pharmaceutical composition according to claim 1, wherein the polynucleotide comprises a sequence GTATTTCCCAGAAAAGGAAC (SEQ ID NO:21).

16. The pharmaceutical composition according to claim 1, wherein the polynucleotide comprises a sequence AAGCGAAAATGAAATTGACT (SEQ ID NO:22).

17. The pharmaceutical composition according to claim 1, wherein the polynucleotide comprises a sequence CAGGCATAACGGTTCCGTAG (SEQ ID NO:23).

18. The pharmaceutical composition according to claim 1, wherein the polynucleotide is an oligonucleotide consisting of a sequence GATTGCCTGACGTCAGAGAG (SEQ ID NO:8).

19. The pharmaceutical composition according to claim 1, wherein the polynucleotide is an oligonucleotide consisting of a sequence GGAATGACGTTCCCTGTG (SEQ ID NO:9).

20. The pharmaceutical composition according to claim 1, wherein the polynucleotide is an oligonucleotide consisting of a sequence AGCTATGACGTTCCAAGG (SEQ ID NO:10).

21. The pharmaceutical composition according to claim 1, wherein the polynucleotide is an oligonucleotide consisting of a sequence GCTTGATGACTCAGCCGGAA (SEQ ID NO:11).

22. The pharmaceutical composition according to claim 1, wherein the polynucleotide is an oligonucleotide consisting of a sequence TCGATCGGGGCGGGGCGAGC (SEQ ID NO:12).

23. The pharmaceutical composition according to claim 1, wherein the polynucleotide is an oligonucleotide consisting of a sequence TGCAGATTGCGCAATCTGCA (SEQ ID NO:13).

24. The pharmaceutical composition according to claim 1, wherein the polynucleotide is an oligonucleotide consisting of a sequence AGCGGGGGCGAGCGGGGGCG (SEQ ID NO:14).

25. The pharmaceutical composition according to claim 1, wherein the polynucleotide is an oligonucleotide consisting of a sequence GTCCATTTCCCGTAAATCTT (SEQ ID NO:16).

26. The pharmaceutical composition according to claim 1, wherein the polynucleotide is an oligonucleotide consisting of a sequence TATGCATATTCCTGTAAGTG (SEQ ID NO:17).

27. The pharmaceutical composition according to claim 1, wherein the polynucleotide is an oligonucleotide consisting of a sequence CTGATTTCCCCGAAATGATG (SEQ ID NO:19).

28. The pharmaceutical composition according to claim 1, wherein the polynucleotide is an oligonucleotide consisting of a sequence AGATTTCTAGGAATTCAATC (SEQ ID NO:20).

29. The pharmaceutical composition according to claim 1, wherein the polynucleotide is an oligonucleotide consisting of a sequence GTATTTCCCAGAAAAGGAAC (SEQ ID NO:21).

30. The pharmaceutical composition according to claim 1, wherein the polynucleotide is an oligonucleotide consisting of a sequence AAGCGAAAATGAAATTGACT (SEQ ID NO:22).

31. The pharmaceutical composition according to claim 1, wherein the polynucleotide is an oligonucleotide consisting of a sequence CAGGCATAACGGTTCCGTAG (SEQ ID NO:23).

32. The pharmaceutical composition according to any one of claims 4–17, wherein the polynucleotide comprises at least one phosphorothioate linkage.

33. The pharmaceutical composition according to any one of claims 18–31, wherein the oligonucleotide comprises at least one phosphorothioate linkage.

34. The pharmaceutical composition according to any one of claims 4–31, wherein the antigen is selected from the group consisting of peptides, polypeptides, proteins, polysaccharides, steroids, tumor cell antigens, and tumor cells.

* * * * *

UNITED STATES PATENT AND TRADEMARK OFFICE
CERTIFICATE OF CORRECTION

PATENT NO. : 7,001,890 B1
DATED : February 21, 2006
INVENTOR(S) : Hermann Wagner et al.

It is certified that error appears in the above-identified patent and that said Letters Patent is hereby corrected as shown below:

Column 12,
Line 43, insert the following:

Table 2 Sequences of oligomers and death due to lethal shock a

| | | | |
|---|---|---|---|
| 1668 | TCCA<u>TGACGTT</u>CCTGATGCT | | (SEQ ID NO: 4) |
| CRE | ATTGCC<u>TGACGTCA</u>GAGAGC | | (SEQ ID NO: 5) |
| 1668-CA | TCCA<u>TGACGTCA</u>CTGATGCT | | (SEQ ID NO: 6) |
| CRE-TC | ATTGCC<u>TGACGTTC</u>GAGAGC | | (SEQ ID NO: 7) | b

| | |
|---|---|
| 1668 | 5/5 |
| CRE | 0/5 |
| 1668-CA | 0/3 |
| CRE-TC | 3/3 |

Lethality was determined as in Example 2. The 1668 sequence fortuitously contains a combination of transcription response elements, namely the transcription factor binding sites (TGACGTTCC). This element represents the binding site for HSVIP04 (ATF), HSINS04 (CREB half site), CAMV35SR03 (HBP-1a yeast) or ADE422 (AP-1) in combination with an HSIL606 site which is a repressor site (sequence analysis from EMBL database Heidelberg). This sequence can be found in the 5' non-coding regions (promoters) of several eukaryotic cytokine genes including human IL-13 promoter and IL-12 p40 intron 1. The CRE sequence contains all the response elements cited above except for HSIL606 and it contains the full CRE palindromic sequence (TGACGTCA). In accordance with the invention, the CRE sequence did not induce death and changes in the 1668 eliminate toxicity.

TNF-$\alpha$ release is a hallmark of lethal toxic shock [Tracey, K. J. et al., Science 234, 470-474 (1986), Tracey, K. J. et al., Nature 330, 662-664 (1987)]. An exchange of only two nucleotides between CRE and 1668 resulted in a loss of macrophage induced TNF-$\alpha$ release activity. The sequence of the corresponding oligonucleotide is given in Table 2. The reported 6-mer active core sequence of 1668 contains the CpG flanked by two 5' purines and two 3' pyrimidines. The exchange of CA for TC does not affect this motif, however, TNF-$\alpha$ release was severely diminished. Thus, the broader core 8-mer sequence or the transcription response element and not the surrounding sequence environment was responsible for these effects. In accordance with the invention, when utilizing macrophage derived TNF-$\alpha$ release as a marker, the information comprised in the prior art 5'Pu-Pu-CpG-Py-Py-3' motif alone was not satisfactory for predicting oligomer activity or toxicity. Additionally, in contrast to 1668, CRE did not induce IL-6 release in vivo or from the ANA-1 cell line in vitro.

UNITED STATES PATENT AND TRADEMARK OFFICE
CERTIFICATE OF CORRECTION

PATENT NO. : 7,001,890 B1
DATED : February 21, 2006
INVENTOR(S) : Hermann Wagner et al.

It is certified that error appears in the above-identified patent and that said Letters Patent is hereby corrected as shown below:

<u>Column 13,</u>
Line 49, the title of Table 4, "Sequence of ukary tic TRE te t d" should read
-- Sequences of eukaryotic TRE tested --.
Line 58, Table 4, "STAT 4   CTGATTTCCCCGAAATGATG   (SEQ ID NO: 19)"
should read -- STAT 4   CTGATTTCCCCGAAATGATG   (SEQ ID NO: 19) --.

Signed and Sealed this

Thirtieth Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 7,001,890 B1  Page 1 of 2
APPLICATION NO. : 09/355254
DATED : February 21, 2006
INVENTOR(S) : Hermann Wagner et al.

It is certified that error appears in the above-identified patent and that said Letters Patent is hereby corrected as shown below:

Column 12,
Line 43, insert the following:

Table 2 Sequences of oligomers and death due to lethal shock a

| | | |
|---|---|---|
| 1668 | TCCA<u>TGACGTT</u>CCTGATGCT | (SEQ ID NO: 4) |
| CRE | ATTGCC<u>TGACGTCA</u>GAGAGC | (SEQ ID NO: 5) |
| 1668-CA | TCCA<u>TGACGTCA</u>CTGATGCT | (SEQ ID NO: 6) |
| CRE-TC | *ATTGCC<u>TGACGTTC</u>GAGAGC* | (SEQ ID NO: 7) | b

| | |
|---|---|
| 1668 | 5/5 |
| CRE | 0/5 |
| 1668-CA | 0/3 |
| CRE-TC | 3/3 |

Lethality was determined as in Example 2. The 1668 sequence fortuitously contains a combination of transcription response elements, namely the transcription factor binding sites (TGACGTTCC). This element represents the binding site for HSVIP04 (ATF), HSINS04 (CREB half site), CAMV35SR03 (HBP-1a yeast) or ADE422 (AP-1) in combination with an HSIL606 site which is a repressor site (sequence analysis from EMBL database Heidelberg). This sequence can be found in the 5' non-coding regions (promoters) of several eukaryotic cytokine genes including human IL-13 promoter and IL-12 p40 intron 1. The CRE sequence contains all the response elements cited above except for HSIL606 and it contains the full CRE palindromic sequence (TGACGTCA). In accordance with the invention, the CRE sequence did not induce death and changes in the 1668 eliminate toxicity.

TNF-$\alpha$ release is a hallmark of lethal toxic shock [Tracey, K. J. et al., Science 234, 470-474 (1986), Tracey, K. J. et al., Nature 330, 662-664 (1987)]. An exchange of only two nucleotides between CRE and 1668 resulted in a loss of macrophage induced TNF-$\alpha$ release activity. The sequence of the corresponding oligonucleotide is given in Table 2. The reported 6-mer active core sequence of 1668 contains the CpG flanked by two 5' purines and two 3' pyrimidines. The exchange of CA for TC does not affect this motif, however, TNF-$\alpha$ release was severely diminished. Thus, the broader core 8-mer sequence or the transcription response element and not the surrounding sequence environment was responsible for these effects. In accordance with the invention, when utilizing macrophage derived TNF-$\alpha$ release as a marker, the information comprised in the prior art 5'Pu-Pu-CpG-Py-Py-3' motif alone was not satisfactory for predicting oligomer activity or toxicity. Additionally, in contrast to 1668, CRE did not induce IL-6 release in vivo or from the ANA-1 cell line in vitro.

UNITED STATES PATENT AND TRADEMARK OFFICE
CERTIFICATE OF CORRECTION

PATENT NO. : 7,001,890 B1
APPLICATION NO. : 09/355254
DATED : February 21, 2006
INVENTOR(S) : Hermann Wagner et al.

It is certified that error appears in the above-identified patent and that said Letters Patent is hereby corrected as shown below:

Column 13,
Line 49, the title of Table 4, "Sequence of ukary tic TRE te t d" should read
-- Sequences of eukaryotic TRE tested --.
Line 58, Table 4, "STAT 4   CTGATTTCCCCGAAATGATG   (SEQ ID NO: 19)"
should read -- STAT 4   CTGATTTCCCCGAAATGATG   (SEQ ID NO: 19) --.

This certificate supersedes Certificate of Correction issued May 30, 2006.

Signed and Sealed this

Tenth Day of October, 2006

JON W. DUDAS
*Director of the United States Patent and Trademark Office*

SEQUENCE LISTING

<160> NUMBER OF SEQ ID NOS: 27

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
tcattggaaa acgttcttcg gggc                                      24

<210> SEQ ID NO 2
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 2
accgatgacg tcgccggtga cggcaccacg                                30

<210> SEQ ID NO 3
<211> LENGTH: 8
<212> TYPE: PRT
<213> ORGANISM: Artificial sequence
<220> FEATURE:
<223> OTHER INFORMATION: Synthetic oligopeptide

<400> SEQUENCE: 3

Ser Ile Ile Asn Phe Glu Lys Leu
1               5

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 4
tccatgacgt tcctgatgct                                              20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
attgcctgac gtcagagagc                                              20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tccatgacgt cactgatgct                                              20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
attgcctgac gttcgagagc                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
gattgcctga cgtcagagag                                              20

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 9
ggaatgacgt tccctgtg                                                18

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
agctatgacg ttccaagg                                                18
```

-continued

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
gcttgatgac tcagccggaa                                                20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
tcgatcgggg cggggcgagc                                                20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tgcagattgc gcaatctgca                                                20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14 agcggggggcg agcggggggcg                                              20

<210> SEQ ID NO 15
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 15
tactttcagt ttcatattac tcta                                           24

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
gtccatttcc cgtaaatctt                                                20

<210> SEQ ID NO 17
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 17
tatgcatatt cctgtaagtg                                          20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
gatccttctg ggaattccta                                          20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ctgatttccc cgaaatgatg                                          20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agatttctag gaattcaatc                                          20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
gtatttccca gaaaaggaac                                          20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
aagcgaaaat gaaattgact                                          20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
caggcataac ggttccgtag                                          20
```

```
<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24 atataggga aatttccagc                                                    20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
caaaaaaatt tccagtcctt                                                   20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
atgttttcct gcgttgccag                                                   20

<210> SEQ ID NO 27
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 27
ctctgacgtc agggaaatt tccagc                                             26
```